US012421538B2

(12) United States Patent
Derosa et al.

(10) Patent No.: US 12,421,538 B2
(45) Date of Patent: *Sep. 23, 2025

(54) QUANTITATIVE ASSESSMENT FOR CAP EFFICIENCY OF MESSENGER RNA

(71) Applicant: TRANSLATE BIO, INC., Lexington, MA (US)

(72) Inventors: Frank Derosa, Lexington, MA (US); Anusha Dias, Lexington, MA (US); Michael Heartlein, Lexington, MA (US)

(73) Assignee: TRANSLATE BIO, INC., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/430,247

(22) Filed: Feb. 1, 2024

(65) Prior Publication Data
US 2024/0417774 A1    Dec. 19, 2024

Related U.S. Application Data

(63) Continuation of application No. 17/325,092, filed on May 19, 2021, now Pat. No. 11,920,182, which is a continuation of application No. 16/744,985, filed on Jan. 16, 2020, now Pat. No. 11,104,934, which is a continuation of application No. 14/775,844, filed as application No. PCT/US2014/027602 on Mar. 14, 2014, now Pat. No. 10,626,439.

(60) Provisional application No. 61/784,253, filed on Mar. 14, 2013.

(51) Int. Cl.
*C12Q 1/68* (2018.01)
*C12Q 1/6804* (2018.01)

(52) U.S. Cl.
CPC .................. *C12Q 1/6804* (2013.01)

(58) Field of Classification Search
CPC .................................................. C12Q 1/6804
See application file for complete search history.

(56) References Cited

U.S. PATENT DOCUMENTS

| | | | |
|---|---|---|---|
| 9,970,047 | B2 | 5/2018 | Heartlein et al. |
| 10,626,439 | B2 | 4/2020 | Heartlein et al. |
| 11,104,934 | B2 | 8/2021 | Heartlein et al. |
| 11,365,437 | B2 | 6/2022 | Heartlein et al. |
| 11,920,182 | B2 * | 3/2024 | Heartlein ............. C12Q 1/6804 |
| 2002/0197622 | A1 | 12/2002 | McDevitt et al. |
| 2005/0053942 | A1 | 3/2005 | Kauppinen et al. |
| 2010/0035249 | A1 | 2/2010 | Hayashizaki et al. |
| 2012/0251618 | A1 | 10/2012 | Schrum et al. |
| 2016/0002705 | A1 | 1/2016 | Heartlein et al. |
| 2016/0032356 | A1 | 2/2016 | Heartlein et al. |
| 2018/0291425 | A1 | 10/2018 | Heartlein et al. |
| 2020/0318156 | A1 | 10/2020 | Heartlein et al. |
| 2022/0364145 | A1 | 11/2022 | DeRosa et al. |

FOREIGN PATENT DOCUMENTS

| | | |
|---|---|---|
| WO | 2017149139 A1 | 9/2017 |
| WO | 2019207060 A1 | 10/2019 |

OTHER PUBLICATIONS

Tilkorn, A. (Authorized Officer), Written Opinion of the International Searching Authority for PCT/US2014/027587 dated Jul. 24, 2014, 4 pages.
Kore et al., "Synthesis and biological evaluation of trimethyl-substituted cap analogs", Bioorganic & Medicinal Chemistry, 2008, vol. 18, No. 3, pp. 880-884.
Gall-Truchot, A. (Authorized Officer), International Search Report for PCT/US2014/027602 dated Jul. 28, 2014, 6 pages.
Tilkorn, A. (Authorized Officer), International Search Report for PCT/US2014/027587 dated Jul. 24, 2014, 6 pages.
Albers et al., "Analysis of mRNA 5'-Terminal Cap Structures and Internal N6-Methyladenosine by Reversed-Phase High-Performance Liquid Chromatography", Analytical Biochemistry, 1981, vol. 113, pp. 118-123.
Nojima et al., "The Interaction between cap-binding complex and RNA export factor is required for intronless mRNA export", Journal of Biological Chemistry, 2007, vol. 282, No. 21, pp. 15645-15651.
Tcherepanova et al., "Ectopic expression of a truncated CD40L protein from synthetic post-transcriptionally capped RNA in dendritic cells induces high levels of IL-12 secretion", BMC Molecular Biology, 2008, 9:90, 13 pages.
Grudzien et al., "Novel cap analogs for in vitro synthesis of mRNAs with high translational efficiency", RNA, 2004, vol. 10, No. 9, pp. 1479-1487.
Theus et al., "A Simple Assay for Determining the Capping Efficiencies of RNA Polymerases Used for In Vitro Transcription", Biotechniques, 1990, vol. 9, No. 5, pp. 610-612 and 614-615.
McCracken et al., "5'-Capping enzymes are targeted to pre-mRNA by binding to the phosphorylated carboxy-terminal domain of RNA polymerase II", Genes and Development, 1997, vol. 22, No. 24, pp. 3306-3318.
Gall-Truchot, A. (Authorized Officer), Written Opinion of the International Searching Authority for PCT/US2014/027602 dated Jul. 28, 2014, 6 pages.

(Continued)

*Primary Examiner* — Jezia Riley
(74) *Attorney, Agent, or Firm* — MH2 Technology Law Group, LLP

(57) ABSTRACT

The present invention provides, among other things, methods of quantitating mRNA capping efficiency, particularly mRNA synthesized in vitro. In some embodiments, methods according to the present invention comprise providing an mRNA sample containing capped and uncapped mRNA, providing a cap specific binding substance under conditions that permit the formation of a complex between the cap specific binding substance and the capped mRNA, and quantitatively determining the amount of the complex as compared to a control, thereby quantifying mRNA capping efficiency.

21 Claims, 5 Drawing Sheets
Specification includes a Sequence Listing.

(56) References Cited

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", No. 3.5 of "Efficacy and Mechanism Evaluation", Southampton (UK), NIHR Journals Library, 2016.
Jemielity et al., "Novel 'anti-reverse' cap analogs with superior translational properties", RNA, 2003, vol. 9, No. 9, pp. 1108-1122.
Otsuka et al., "Identification of a cytoplasmic complex that adds a cap onto 5'-monophosphate RNA", Molecular and Cellular Biology, 2009, vol. 29, No. 8, pp. 2155-2167.
Kore et al., "Synthesis and evaluation of 2'-O-allyl substituted dinucleotide cap analog for mRNA translation", Bioorganic & Medicinal Chemistry, 2010, vol. 18, No. 22, pp. 8061-8065.
Galipon et al., "Stress-induced lncRNAs evade nuclear degradation and enter the translational machinery", Genes to Cells, 2013, vol. 18, No. 5, pp. 353-368.
US Notice of Allowance dated Feb. 22, 2022 for U.S. Appl. No. 15/936,293, 13 pages.
US Notice of Allowance dated Jan. 8, 2018 for U.S. Appl. No. 14/775,846, 8 pages.
US Office Action dated Mar. 19, 2020 for U.S. Appl. No. 15/936,293, 11 pages.
US Office Action dated Jun. 2, 2017 for U.S. Appl. No. 14/775,846, 16 pages.
US Office Action dated Feb. 26, 2021 for U.S. Appl. No. 15/936,293, 13 pages.
US Office Action dated Sep. 3, 2020 for U.S. Appl. No. 15/936,293, 14 pages.
US Office Action dated Oct. 4, 2017 for U.S. Appl. No. 14/775,846, 5 pages.
US Office Action dated Jul. 19, 2023 for U.S. Appl. No. 17/746,657, 15 pages.
Huang, Z., et al., "Single-nucleotide resolution of RNAs up to 59 nucleotides by high-performance liquid chromatography," Analytical Biochemistry, 2013 (Available Online Dec. 27, 2012), vol. 435, pp. 35-43.
Wisniewski, M., et al., "Substrate Requirements for Secondary Cleavage by HIV-1 Reverse Transcriptase RNase H," The Journal of Biological Chemistry, 2002 (Originally Published Online May 21, 2002), vol. 277, No. 32, pp. 28400-28410 (12 pages total).
Moteki, S., et al., "Functional Coupling of Capping and Transcription of mRNA", Molecular Cell, 2002, vol. 10, No. 3, pp. 559-609.
Office Action dated Aug. 25, 2023 for corresponding European Patent Application No. 18207398.1, 5 pages.
Anonymous: "Monoclonal mouse antibody against m3G-cap/m7G-cap", Synaptic Systems GmbH Retrieved from the Internet: URL:https://www.sysy.com/products/cap/facts-201011.pbp, 2 pages.
Luhrmann et al., "Isolation and characterization of rabbit anti-m227G antibodies", Nucleic Acids Research, 1982, vol. 10, No. 22, pp. 7103-7113.
Meredith et al., "Isolation and characterization of rabbit anti-m7G-5'-P antibodies of high apparent affinity", Nucleic Acids Research, 1979, vol. 6, No. 6, pp. 2179-2191.

\* cited by examiner

A.

B.

C.

SEQUENCE LISTING

```
Sequence total quantity: 8
SEQ ID NO: 1                moltype = RNA   length = 582
FEATURE                     Location/Qualifiers
source                      1..582
                            mol_type = mRNA
                            organism = Homo sapiens
SEQUENCE: 1
atggggtgc acgaatgtcc tgcctggctg tggcttctcc tgtccctgct gtcgctccct    60
ctgggcctcc cagtcctggg cgccccacca cgcctcatct gtgacagccg agtcctggaa   120
aggtacctct tggaggccaa ggaggccgag aatatcacga cgggctgtgc tgaacactgc   180
agcttgaatg agaatatcac tgtcccagac accaaagtta atttctatgc ctggaagagg   240
atggaggtcg ggcagcaggc cgtagaagtc tggcagggcc tggccctgct gtcggaagct   300
gtcctgcggg gccaggccct gttggtcaac tcttcccagc cgtgggagcc cctgcagctg   360
catgtggata aagccgtcag tggccttcgc agcctcacca ctctgcttcg ggctctggga   420
gcccagaagg aagccatctc ccctccagat gcggcctcag ctgctccact ccgaacaatc   480
actgctgaca ctttccgcaa actcttccga gtctactcca atttccggg ggaaagctg    540
aagctgtaca caggggaggc ctgcaggaca ggggacagat ga                     582

SEQ ID NO: 2                moltype = RNA   length = 1652
FEATURE                     Location/Qualifiers
misc_feature                1..1652
                            note = Synthetic polynucleotide
source                      1..1652
                            mol_type = other RNA
                            organism = synthetic construct
SEQUENCE: 2
atggaagatg ccaaaaacat taagaagggc ccagcgccat tctacccact cgaagacggg    60
accgccggcg agcagctgca caaagccatg aagcgctacg ccctggtgcc cggcaccatc   120
gcctttaccg acgcacatat cgaggtggac attacctacg ccgagtactt cgagatgagc   180
gttcggctgg cagaagctat gaagcgctat gggctgaata caaaccatcg gatcgtggtg   240
tgcagcgaga atagcttgca gttcttcatg cccgtgttgg gtgccctgtt catcggtgtg   300
gctgtggccc cagctaacga catctacaac gagcgcgagc tgctgaacag catgggcatc   360
agccagccca ccgtcgtatt cgtgagcaag aaagggctgc aaaagatcct caacgtgcaa   420
aagaagctac cgatcgcataca aaagatcatc atcatggata gcaagaccga ctaccagggc   480
ttccaaagca tgtacacctt cgtgacttcc catttgccac ccggcttcaa cgagtacgac   540
ttcgtgcccg agagcttcga ccgggacaaa accatcgctc tgatcatgaa cagtagtggc   600
agtaccggat tgcccaaggg cgtagcccta ccgcaccgca ccgcttgtgt ccgattcagt   660
catgcccgcg accccatctt cggcaaccag atcatccccg acaccgctat cctcagcgtg   720
gtgccatttc accacggctt cggcatgttc accacgctgg gctacttgat ctgcggcttt   780
cgggtcgtgc tcatgtaccg cttcgaggag gagctattct tgcgcagctt gcaagactat   840
aagattcaat ctgccctgct ggtgcccaca ctatttagct tcttcgctaa gagcactctc   900
atcgacaagt acgaccttaag caacttgcac gagatcgcca gcggcgggc gccgctcagc   960
aaggaggtag tgaggccgt ggccaaacgc ttccacctac aggcatccg ccagggctac    1020
ggcctgacag aaacaaccag cgccattctg atcacccccg aagggacga caagcctgcc   1080
gcagtaggca aggtggtgcc cttcttcgag gctaaggtgg tggacttgga caccggtaag   1140
acactgggtg tgaaccagcg cggcgagctg tgcgtccgtg gccccatgat catgagcggc   1200
tacgttaaca accccgaggc tacaaacgct ctcatcgaca ggacggctg gctgcacagc   1260
ggcgacatcg cctactggga cgaggacgga cacttcttca tcgtggaccg gctgaagagc   1320
ctgatcaaat acaagggcta ccaggtagcc ccagccgaac tggagagcat cctgctgcaa   1380
cacccaaca tcttcgacgc cggggtcgcc ggcctgcccg acgacgatgc cggcgagctg   1440
cccgccgcag tcgtcgtgct ggaacacggt aaaaccatga ccgagaagga gatcgtggac   1500
tatgtggcca gccaggttac aaccgccaag aagctgcgcg gtggtgttgt gttcgtggac   1560
gaggtgccta aaggactgac cggcaagttg gacgcccgca gatccgcga gattctcatt   1620
aaggccaaga agggcggcaa gatcgccgtg ta                                1652

SEQ ID NO: 3                moltype = RNA   length = 140
FEATURE                     Location/Qualifiers
misc_feature                1..140
                            note = Synthetic polynucleotide
source                      1..140
                            mol_type = other RNA
                            organism = synthetic construct
SEQUENCE: 3
ggacagatcg cctggagacg ccatccacgc tgttttgacc tccatagaag acaccgggac    60
cgatccagcc tccgcggccg ggaacggtgc attggaacgc ggattccccg tgccaagagt   120
gactcaccgt ccttgacacg                                               140

SEQ ID NO: 4                moltype = RNA   length = 11
FEATURE                     Location/Qualifiers
misc_feature                1..11
                            note = Synthetic polynucleotide
source                      1..11
                            mol_type = other RNA
                            organism = synthetic construct
SEQUENCE: 4
gggatcctac c                                                         11

SEQ ID NO: 5                moltype = RNA   length = 100
```

| FEATURE | Location/Qualifiers |
|---|---|
| misc_feature | 1..100 |
| | note = Synthetic polynucleotide |
| source | 1..100 |
| | mol_type = other RNA |
| | organism = synthetic construct |

SEQUENCE: 5

```
cgggtggcat ccctgtgacc cctccccagt gcctctcctg gccctggaag ttgccactcc   60
agtgcccacc agccttgtcc taataaaatt aagttgcatc                        100
```

| SEQ ID NO: 6 | moltype =   length = |
|---|---|
| SEQUENCE: 6 | |
| 000 | |

| SEQ ID NO: 7 | moltype = RNA   length = 1290 |
|---|---|
| FEATURE | Location/Qualifiers |
| misc_feature | 1..1290 |
| | note = Synthetic polynucleotide |
| source | 1..1290 |
| | mol_type = other RNA |
| | organism = synthetic construct |

SEQUENCE: 7

```
atgcagctga ggaacccaga actacatctg gctgcgcgc ttgcgcttcg cttcctggcc     60
ctcgtttcct gggacatccc tggggctaga gcactggaca atggattggc aaggacgcct   120
accatgggct ggctgcactg ggagcgcttc atgtgcaacc ttgactgcca ggaagagcca   180
gattcctgca tcagtgagaa gctcttcatg gagatggcag agctcatggt ctcagaaggc   240
tggaaggatg caggttatga gtacctctgc attgatgact gttggatggc tccccaaaga   300
gattcagaag gcagacttca ggcagaccct cagcgctttc ctcatgggat cgccagcta   360
gctaattatg ttcacagcaa aggactgaag ctagggattt agcagatgt tggaaataaa   420
acctgcgcag gcttccctgg agttttgga tactacgaca ttgatgccca gaccttgct     480
gactggggag tagatctgct aaaatttgat ggttgttact gtgacagttt ggaaaatttg   540
gcagatggtt ataagcacat gtccttggcc ctgaataga ctggcagaag cattgtgtac    600
tcctgtgagt ggcctcttta tatgtggccc tttcaaaagc ccaattatac agaaatccga   660
cagtactgca aaattttgct gacattgatg attcctggaa aagtataaag                720
agtatcttgg actggacatc ttttaaccag agagagaattg ttgatgttgc tggaccaggg   780
ggttggaatg acccagatat gttagtgatt ggcaactttg gcctcagctg gaatcagcaa   840
gtaactcaga tggcccctg gctatatcatg gctgctcctt tattcatgtc taatgacctc   900
cgacacatca gccctcaagc caaagctctc cttcaggata aggacgtaat tgccatcaat   960
caggaccctg ggcaagca agggtaccag cttagacagg gagacaactt tgaagtgtgg  1020
gaacgacctc tctcaggctt agcctgggct gtagctatga taaaccggca ggagattggt  1080
ggacctcgct cttataccat cgcagttgct tccctgggta aaggagtggc ctgtaatcct  1140
gcctgcttca tcacacagct cctccctgtg aaaaggaagc tagggttcta tgaatggact  1200
tcaaggttaa gaagtcacat aaatcccaca ggcactgttt tgcttcagct agaaaataca  1260
atgcagatgt cattaaaaga cttactttaa                                    1290
```

| SEQ ID NO: 8 | moltype = RNA   length = 1510 |
|---|---|
| FEATURE | Location/Qualifiers |
| misc_feature | 1..1510 |
| | note = Synthetic polynucleotide |
| source | 1..1510 |
| | mol_type = other RNA |
| | organism = synthetic construct |

SEQUENCE: 8

```
atgcagctga ggaacccaga gctccatctc ggatgtgcac tggcacttag atttctcgcg    60
cttgtgtcgt gggacatccc cggagccagg gcgctggata atggattgge gcggactcgc   120
acaatgggtt ggctgcactg ggagcgcttt atgtgcaatc tggactgcca ggaagagccc   180
gatagctgta tttcggagaa gctcttcatg gaaatggcgg agttgatggt gtccgaaggg   240
tggaaggatg cgggatatga gtatctgtgt atcgatgact gctggatggc accgcagcga   300
gattcggagg ggcgattgca ggccgaccct cagcgcttcc ctcatggaat tcggcagctg   360
gccaactacg tacactcaaa aggacttaag ttggggatct acgcggacgt cggtaataag   420
acatgcgctg ggttcccggg gagcttcgga tactatgata ttgatgccca gaccttcgcg   480
gactggggag tggacttgct taagtttgat ggttgttact gtgactcatt ggaaaacttg   540
gcggatgggt ataaacatat gtccttggcc ttgaatcgga cagggcgtc gatcgtctac    600
agctgcgaat ggccttttgta tatgtggccg ttccagaaac ccaactacac cgaaattcgc   660
cagtattgca aaatcactgg agaaacttcg ccgatatcac attcgtggaa atcaatcaag   720
tccatcctcg actggacgtc cttcaaccaa gagagaatcg tagatgtgc cggaccgagg   780
ggatggaacg accctgatat gcttgtaatt ggcaactttg gactctcgtg aaccagcaa    840
gtaacgcaaa tggcactctg gctatatcatg gctgcgcccc tgttcatgtc aaacgacctc   900
aggcacatct cgccgcaggc gaaagccttg cttcaagata aggacgtcat cgcgattaat   960
caggacccgc tggggaagca gggctatcag cttagacagg gcgacaattt tgaggtctgg  1020
gagcgaccc tgacggact gcatggccg gtggcaatga tcaataggca ggaaattggt  1080
gggccgaggt cgtacactat cgccgtcgcg tcgttgggaa agggtgtggc gtgtaatcca  1140
gcgtgcttta tcacccaact gctgccgtc aagcgcaaac tgggtttta cgaatggacg  1200
agcagacttc gctcacacat taacccaacg ggtacggtgt tgctccagct cgagaataca  1260
atgcaaatgt cacttaaaga tttgctctga cgggtggcat ccctgtgacc cctccccagt  1320
gcctctcctg gccctggaag ttgccactcc agtgcccacc agccttgtcc taataaaatt  1380
```

```
aagttgcatc aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaaaaaaa aaaaaaaaaa    1500
aaaaaaaaaa                                                           1510
```

QUANTITATIVE ASSESSMENT FOR CAP EFFICIENCY OF MESSENGER RNA

CROSS-REFERENCE TO RELATED APPLICATIONS

This application is a continuation application of U.S. application Ser. No. 17/325,092 filed May 19, 2021, which is a continuation application of U.S. application Ser. No. 16/744,985 filed Jan. 16, 2020 (now U.S. Pat. No. 11,104,934), which is a continuation application of U.S. application Ser. No. 14/775,844 filed Sep. 14, 2015 (now U.S. Pat. No. 10,626,439), which is a U.S. national stage entry of International Application No. PCT/US14/27602 filed Mar. 14, 2014, which claims priority to U.S. provisional patent application No. 61/784,253 filed Mar. 14, 2013, the disclosures of each of which are hereby incorporated in their entirety.

INCORPORATION BY REFERENCE OF SEQUENCE LISTING

This instant application contains a Sequence Listing which has been filed electronically in XML format and is hereby incorporated by reference in its entirety. Said XML copy created on 1 Feb. 2024 is named "0171-0087-PCT-US-CON3_SL.xml" and is 14,908 bytes in size.

BACKGROUND

Messenger RNA ("mRNA") therapy is becoming an increasingly important approach for the treatment of a variety of diseases. Effective mRNA therapy requires effective delivery of the mRNA to the patient and efficient production of the protein encoded by the mRNA within the patient's body. To optimize mRNA delivery and protein production in vivo, a proper cap are typically required at the 5' end of the construct, which protects the mRNA from degradation and facilitates successful protein translation. Therefore, accurate characterization of the capping efficiency is particularly important for determining the quality of mRNA for therapeutic applications.

SUMMARY OF THE INVENTION

The present invention provides improved methods for accurately and quantitatively determining the capping efficiency of mRNA, in particular, mRNA synthesized in vitro. As discussed above, proper capping is important for successful protein production in vivo. However, prior to the present invention, most cap assays are qualitative, which is not sufficient for assessing the quality of an mRNA based therapeutic product and related safety and efficacy for in vivo use. In fact, prior to the present invention, there is no method available that allows quantification of capping efficiency without permanent alterations of the mRNAs in a sample. As described in detail below, the present invention is, in part, based on the formation and quantification of a complex between a cap specific binding substance (e.g., a cap specific antibody) and a capped mRNA using simple technology such as ELISA. Thus, the present invention provides a simple, reliable and efficient quantitative approach for assessing mRNA capping efficiency. The present invention is particularly useful for quality control during mRNA manufacture and for characterization of mRNA as an active pharmaceutical ingredient (API) in final therapeutic products.

In one aspect, the present invention provides a method of quantifying mRNA capping efficiency, the method comprising steps of providing an mRNA sample containing capped and uncapped mRNA; providing a cap specific binding substance under conditions that permit the formation of a complex between the cap specific binding substance and the capped mRNA; and quantitatively determining the amount of the complex as compared to a control, thereby quantifying mRNA capping efficiency.

In some embodiments, an inventive method of the present invention can be used to quantify a cap having a structure of formula I:

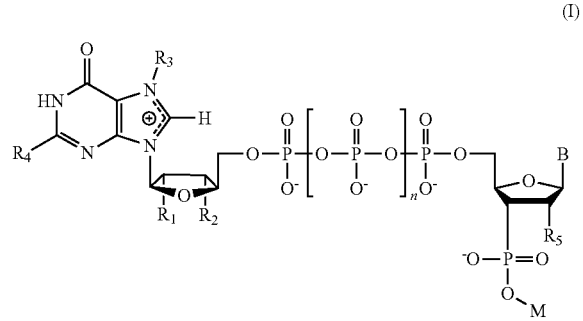

wherein,

B is a nucleobase;

$R_1$ is selected from a halogen, OH, and $OCH_3$;

$R_2$ is selected from H, OH, and $OCH_3$;

$R_3$ is $CH_3$, $CH_2CH_3$, $CH_2CH_2CH_3$ or void;

$R_4$ is $NH_2$;

$R_5$ is selected from OH, $OCH_3$ and a halogen;

n is 1, 2, or 3; and

M is a nucleotide of the mRNA.

In some embodiments, the nucleobase is guanine.

In some embodiments, an inventive method of the present invention can be used to quantify a $m^7G$ cap with a structure of formula II:

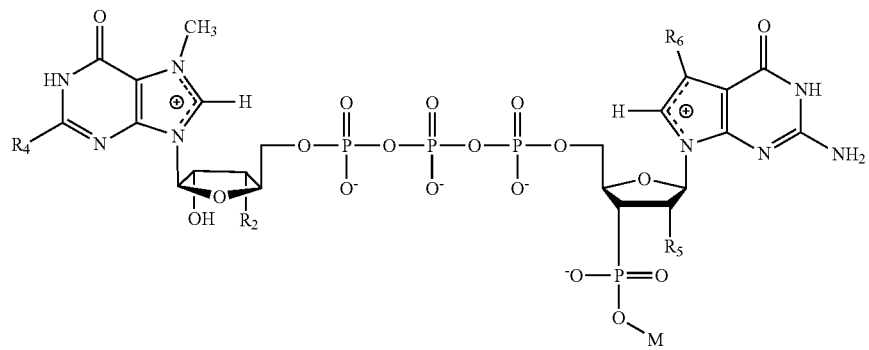

(II)

wherein,
$R_2$ is H or $CH_3$;
$R_4$ is $NH_2$;
$R_5$ is OH or $OCH_3$;
$R_6$ is H or $CH_3$; and
M is a nucleotide of the mRNA.

In some embodiments, a suitable cap specific binding substance is a cap specific binding protein. In some embodiments, a suitable cap specific binding substance is a cap specific antibody. In some embodiments, a suitable cap specific antibody is an anti-$m^7G$ antibody.

In some embodiments, an inventive method according to the present invention involves a step of quantitatively determining the amount of the complex between the cap specific binding substance and the capped mRNA by performing an ELISA assay.

In some embodiments, the step of quantitatively determining the amount of the complex by measuring a detectable signal associated with the complex. In some embodiments, the detectable signal is directly associated with the cap specific binding substance. In some embodiments, the detectable signal is indirectly associated with the cap specific binding substance via a secondary agent that binds the cap specific binding substance. In some embodiments, a suitable secondary agent is a secondary antibody.

In some embodiments, a suitable detectable signal is a fluorescent signal, a colorimetric signal or a radioactive signal. In some embodiments, a suitable fluorescent signal is generated by converting an enzymatic substrate to a chromogenic, chemifluorescent or chemiluminescent product by an enzyme associated directly or indirectly with the cap specific binding substance. In some embodiments, a suitable enzymatic substrate is selected from the groups consisting of p-nitrophenyl phosphate disodium salt (PNPP), 2,2'-Azino-bis [3-ethylbenzothiazoline-6-sulfonic acid]-diammonium salt (ABTS), o-phenylenediamine dihydrochloride (OPD) and 3,3',5,5'-tetramethylbenzidine (TMB). In some embodiments, a suitable enzyme is alkaline phosphatase or horseradish peroxidase.

In some embodiments, a suitable control for quantitative determination is an mRNA sample with a pre-determined amount of capped mRNA. In some embodiments, a suitable control for quantitative determination comprises a predetermined amount of synthesized cap.

In some embodiments, quantifying mRNA capping efficiency comprises quantifying the absolute amount of capped mRNA in the mRNA sample. In some embodiments, quantifying mRNA capping efficiency comprises quantifying the percentage of capped mRNA in the mRNA sample.

In some embodiments, an inventive method according to the present invention further comprises a step of capturing the mRNA on a substrate. In some embodiments, the mRNA is captured by a poly-T oligo that binds to the poly-A tail of the mRNA. In some embodiments, the mRNA is captured by a poly-A binding protein or antibody. In some embodiments, a suitable substrate is a microplate, magnetic bead, particle, polymeric bead, chromatographic resin, filter paper, nitrocellulose, diazocellulose, glass, latex, polystyrene, polyvinylchloride, propylene, polyethylene, dextran, Sepharose, agar, starch, nylon, silica gel, or hydrogel. In some embodiments, the substrate is coated with avidin or streptavidin. In some embodiments, a poly-T oligo or poly-A binding protein or antibody used to capture the mRNA is biotinylated.

In some embodiments, an inventive method according to the present invention is used to quantify mRNA capping efficiency of an mRNA sample synthesized in vitro.

Among other things, the present invention provides compositions and kits for performing inventive methods described herein. In some embodiments, the present invention provides a kit for quantifying mRNA capping efficiency, the kit comprising a cap specific binding substance; one or more reagents for detecting a complex between the cap specific binding substance and a capped mRNA, and a control for quantifying capped mRNA. In some embodiments, a suitable cap specific binding substance is a cap specific antibody. In some embodiments, a suitable cap specific antibody is an anti-$m^7G$ antibody. In some embodiments, a kit of the present invention further contains a substrate to capture mRNA.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWINGS

The drawings are for illustration purposes and are in no way limiting.

DEFINITIONS

Figure 1:
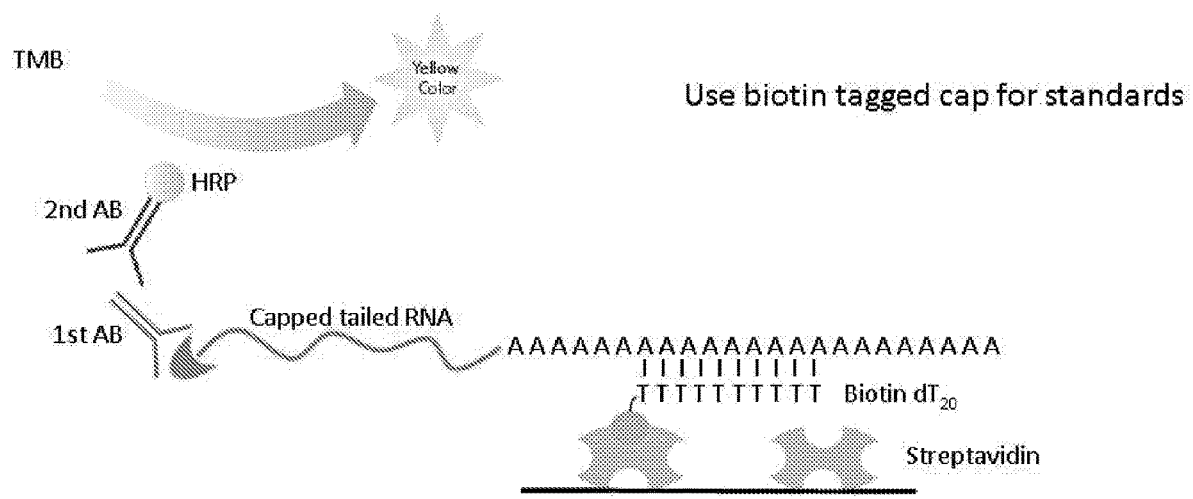
FIG. 1 illustrates an exemplary depiction of a sandwich ELISA-based embodiment of the invention in which a primary mouse monoclonal anti-m⁷G cap antibody specifically binds to the cap of an mRNA. The mRNA has been indirectly captured on a solid substrate via hybridization of its poly(A) tail with a biotinylated oligo-dT primer, which is directly bound to streptavidin coated solid substrate.

In order for the present invention to be more readily understood, certain terms are first defined. Additional definitions for the following terms and other terms are set forth throughout the specification.

Affinity: As is known in the art, "affinity" is a measure of the tightness with which a particular ligand binds to (e.g., associates non-covalently with) and/or the rate or frequency with which it dissociates from, its partner. As is known in the art, any of a variety of technologies can be utilized to determine affinity. In many embodiments, affinity represents a measure of specific binding.

Anneal or hybridization: As used herein, the terms "anneal," "hybridization," and grammatical equivalent, refers to the formation of complexes (also called duplexes or hybrids) between nucleotide sequences which are sufficiently complementary to form complexes via Watson-Crick base pairing or non-canonical base pairing. It will be appreciated that annealing or hybridizing sequences need not have perfect complementary to provide stable hybrids. In many situations, stable hybrids will form where fewer than about 10% of the bases are mismatches. Accordingly, as used herein, the term "complementary" refers to a nucleic acid molecule that forms a stable duplex with its complement under particular conditions, generally where there is about 90% or greater homology (e.g., about 95% or greater, about 98% or greater, or about 99% or greater homology). Those skilled in the art understand how to estimate and adjust the stringency of hybridization conditions such that sequences that have at least a desired level of complementarity will stably hybridize, while those having lower complementarity will not. For examples of hybridization conditions and parameters, see, for example, Sambrook et al., "*Molecular Cloning: A Laboratory Manual*", 1989, Second Edition, Cold Spring Harbor Press: Plainview, NY and Ausubel, "*Current Protocols in Molecular Biology*", 1994, John Wiley & Sons: Secaucus, NJ. Complementarity between two nucleic acid molecules is said to be "complete", "total" or "perfect" if all the nucleic acid's bases are matched, and is said to be "partial" otherwise.

Antibody: As used herein, the term "antibody" refers to a polypeptide consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are typically classified as either kappa or lambda. Heavy chains are typically classified as gamma, mu, alpha, delta, or epsilon, which in turn define the immunoglobulin classes, IgG, IgM, IgA, IgD and IgE, respectively. A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms "variable light chain" (VL) and "variable heavy chain" (VH) refer to these light and heavy chains respectively. An antibody can be specific for a particular antigen (e.g., m⁷G mRNA caps). The antibody or its antigen can be either an analyte or a binding partner. Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of ordinary skill in the art will appreciate that such Fab' fragments may be synthesized de novo either chemically or by utilizing recombinant DNA methodology. Thus, the term "antibody," as used herein also includes antibody fragments either produced by the modification of whole antibodies or synthesized de novo using recombinant DNA methodologies. In some embodiments, antibodies are single chain antibodies, such as single chain Fv (scFv) antibodies in which a variable heavy and a variable light chain are joined together (directly or through a peptide linker) to form a continuous polypeptide. A single chain Fv ("scFv") polypeptide is a covalently linked VH:VL heterodimer which may be expressed from a nucleic acid including VH- and VL-encoding sequences either joined directly or joined by a peptide-encoding linker see, e.g., Huston, et al. (1988) PROC. NAT. ACAD. SCI. USA, 85:5879-5883, the entire contents of which are herein incorporated by reference.). A number of structures exist for converting the naturally aggregated, but chemically separated light and heavy polypeptide chains from an antibody V region into an scFv molecule which will fold into a three dimensional structure substantially similar to the structure of an antigen-binding site. See, e.g. U.S. Pat. Nos. 5,091,513 and 5,132,405 and 4,956,778.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding substance: As used herein, the term "binding substance" includes any molecule, such as a protein (e.g., a peptide, an antibody, etc.), a nucleic acid, an oligonucleotide, a chemical compound, that binds a target (e.g., antigen, a nucleotide, a peptide, a polynucleotide, etc.). A binding substance is also referred to as a capture agent.

Compound and Agent: The terms "compound" and "agent" are used herein interchangeably. They refer to any naturally occurring or non-naturally occurring (i.e., synthetic or recombinant) molecule, such as a biological macromolecule (e.g., nucleic acid, polypeptide or protein), organic or inorganic molecule, or an extract made from biological materials such as bacteria, plants, fungi, or animal (particularly mammalian, including human) cells or tissues. The compound may be a single molecule or a mixture or complex of at least two molecules.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Detectable signal: As used herein, the term "detectable signal" refers to a signal that can be detected or measured by a human being or a machine. In some embodiments, a detectable signal can be quantified such that the intensity of the signal is related to (e.g., proportional to) the amount of the compound associated with the signal. Depending on the nature of the signal, a detectable signal may be detected, measured or quantified by a spectroscopic, photochemical, biochemical, immunochemical, electrical, optical, or chemical means. A "detectable signal" is also referred to as "detectable agent" or "detectable moiety" in this application.

Kit: As used herein, the term "kit" refers to any delivery system for delivering materials. Such delivery systems may include systems that allow for the storage, transport, or delivery of various diagnostic or therapeutic reagents (e.g., oligonucleotides, antibodies, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components in a single container (e.g., in a single box housing each of the desired components). The term "kit" includes both fragmented and combined kits.

Labeled: As used herein, the term "labeled" refers to attachment of a detectable signal, agent or moiety to a compound. See the definition of detectable signal.

Nucleoside: The term "nucleoside" or "nucleobase", as used herein, refers to adenine ("A"), guanine ("G"), cytosine ("C"), uracil ("U"), thymine ("T") and analogs thereof linked to a carbohydrate, for example D-ribose (in RNA) or 2'-deoxy-D-ribose (in DNA), through an N-glycosidic bond between the anomeric carbon of the carbohydrate (1'-carbon atom of the carbohydrate) and the nucleobase. When the nucleobase is purine, e.g., A or G, the ribose sugar is generally attached to the N9-position of the heterocyclic ring of the purine. When the nucleobase is pyrimidine, e.g., C, T or U, the sugar is generally attached to the N1-position of the heterocyclic ring. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR$_2$ or halogen groups, where each R is independently H, C$_1$-C$_6$ alkyl or C$_5$-C$_{14}$ aryl. Ribose examples include ribose, 2'-deoxyribose, 2',3'-dideoxyribose, 2'-haloribose, 2'-fluororibose, 2'-chlororibose, and 2'-alkylribose, e.g., 2'-O-methyl, 4'-alpha-anomeric nucleotides, 1'-alpha-anomeric nucleotides (Asseline et al., Nucl. Acids Res., 19:4067-74 [1991]), 2'-4'- and 3'-4'-linked and other "locked" or "LNA," bicyclic sugar modifications (WO 98/22489; WO 98/39352; WO 99/14226).

Nucleotide: The term "nucleotide" as used herein means a nucleoside in a phosphorylated form (a phosphate ester of a nucleoside), as a monomer unit or within a polynucleotide polymer. "Nucleotide 5'-triphosphate" refers to a nucleotide with a triphosphate ester group at the 5' position, sometimes denoted as "NTP", or "dNTP" and "ddNTP" to particularly point out the structural features of the ribose sugar. The triphosphate ester group may include sulfur substitutions for the various oxygen moieties, e.g., alpha-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry see Shabarova, Z. and Bogdanov, A. Advanced Organic Chemistry of Nucleic Acids, VCH, New York, 1994.

Nucleic acid: The terms "nucleic acid", "nucleic acid molecule", "polynucleotide" or "oligonucleotide" may be used herein interchangeably. They refer to polymers of nucleotide monomers or analogs thereof, such as deoxyribonucleic acid (DNA) and ribonucleic acid (RNA) and combinations thereof. The nucleotides may be genomic, synthetic or semi-synthetic in origin. Unless otherwise stated, the terms encompass nucleic acid-like structures with synthetic backbones, as well as amplification products. As will be appreciated by one skilled in the art, the length of these polymers (i.e., the number of nucleotides it contains) can vary widely, often depending on their intended function or use. Polynucleotides can be linear, branched linear, or circular molecules. Polynucleotides also have associated counter ions, such as H$^+$, NH$_4^+$, trialkylammonium, Mg$^+$, Na$^+$ and the like. A polynucleotide may be composed entirely of deoxyribonucleotides, entirely of ribonucleotides, or chimeric mixtures thereof. Polynucleotides may be composed of internucleotide nucleobase and sugar analogs.

In some embodiments, the term "oligonucleotide" is used herein to denote a polynucleotide that comprises between about 5 and about 150 nucleotides, e.g., between about 10 and about 100 nucleotides, between about 15 and about 75 nucleotides, or between about 15 and about 50 nucleotides. Throughout the specification, whenever an oligonucleotide is represented by a sequence of letters (chosen, for example, from the four base letters: A, C, G, and T, which denote adenosine, cytidine, guanosine, and thymidine, respectively), the nucleotides are presented in the 5' to 3' order from the left to the right. A "polynucleotide sequence" refers to the sequence of nucleotide monomers along the polymer. Unless denoted otherwise, whenever a polynucleotide sequence is represented, it will be understood that the nucleotides are in 5' to 3' orientation from left to right.

Nucleic acids, polynucleotides and oligonucleotides may be comprised of standard nucleotide bases or substituted with nucleotide isoform analogs, including, but not limited to iso-C and iso-G bases, which may hybridize more or less permissibly than standard bases, and which will preferentially hybridize with complementary isoform analog bases. Many such isoform bases are described, for example, by Benner et al., (1987) Cold Spring Harb. Symp. Quant. Biol. 52, 53-63. Analogs of naturally occurring nucleotide monomers include, for example, 7-deazaadenine, 7-deazaguanine, 7-deaza-8-azaguanine, 7-deaza-8-azaadenine, 7-methylguanine, inosine, nebularine, nitropyrrole (Bergstrom, J. Amer. Chem. Soc., 117:1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, 0-6-methylguanine, N-6-methyladenine, O-4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "3'" refers to a region or position in a polynucleotide or oligonucleotide 3' (i.e., downstream) from another region or position in the same polynucleotide or oligonucleotide. The term "5'" refers to a region or position in a polynucleotide or oligonucleotide 5' (i.e., upstream) from another region or position in the same polynucleotide or oligonucleotide. The terms "3' end" and "3' terminus", as used herein in reference to a nucleic acid molecule, refer to the end of the nucleic acid which contains a free hydroxyl group attached to the 3' carbon of the terminal pentose sugar. The term "5' end" and "5' terminus", as used herein in reference to a nucleic acid molecule, refers to the end of the nucleic acid molecule which contains a free hydroxyl or phosphate group attached to the 5' carbon of the terminal pentose sugar. In some embodiments of the invention, oligonucleotide primers comprise tracts of poly-adenosine at their 5' termini.

Primary and secondary antibody: As used herein, the term "primary antibody" typically refers to an antibody that bind a target of interest directly. The term "secondary antibody," as used herein, refers to an antibody that binds another (primary) antibody that, in turn, is bound to a target of interest.

Target: As used herein, the term "target" refers to a molecule of interest.

DETAILED DESCRIPTION

The present invention provides, among other things, improved methods for quantifying mRNA capping efficiency. In some embodiments, the present invention provides a method of quantifying mRNA capping efficiency based on the formation and quantitative determination of a complex between a cap specific binding substance (e.g., a cap specific antibody) and the capped mRNA.

Various embodiments of the present invention are useful in quantitating capping efficiency of in vitro mRNA synthesis. Thus, the present invention provides an important quality control approach for manufacturing mRNA and, in particular, for assessing the safety, efficacy and commercial feasibility of mRNAs with therapeutic applications.

Various aspects of the invention are described in detail in the following sections. The use of sections is not meant to limit the invention. Each section can apply to any aspect of the invention. In this application, the use of "or" means "and/or" unless stated otherwise.

mRNA Capping and/or Methylation

Typically, eukaryotic mRNAs bear a "cap" structure at their 5'-termini, which plays an important role in translation. For example, the cap plays a pivotal role in mRNA metabolism, and is required to varying degrees for processing and maturation of an RNA transcript in the nucleus, transport of mRNA from the nucleus to the cytoplasm, mRNA stability, and efficient translation of the mRNA to protein. The 5' cap structure is involved in the initiation of protein synthesis of eukaryotic cellular and eukaryotic viral mRNAs and in mRNA processing and stability in vivo (see, e.g, Shatkin, A. J., CELL, 9:645-653 (1976); Furuichi, et al., NATURE, 266:235 (1977); FEDERATION OF EXPERIMENTAL BIOLOGISTS SOCIETY LETTER 96:1-11 (1978); Sonenberg, N., PROG. NUC. ACID RES MOL BIOL, 35:173-207 (1988)). Specific cap binding proteins exist that are components of the machinery required for initiation of translation of an mRNA (see, e.g., Shatkin, CELL, 40:223-24 (1985); Sonenberg, N., PROG. NUC. ACID RES MOL BIOL, 35:173-207 (1988)). The cap of mRNA is recognized by the translational initiation factor eIF4E (Gingras, et al., ANN. REV. BIOCHEM. 68:913-963 (1999); Rhoads, R. E., J. BIOL. CHEM. 274:30337-3040, (1999)). The 5' cap structure also provides resistance to 5'-exonuclease activity and its absence results in rapid degradation of the mRNA (see, e.g., Ross, J., MOL. BIOL. MED. 5:1-14 (1988); Green, M. R. et al., CELL, 32:681-694 (1983)). Since the primary transcripts of many eukaryotic cellular genes and eukaryotic viral genes require processing to remove intervening sequences (introns) within the coding regions of these transcripts, the benefit of the cap also extends to stabilization of such pre-mRNA.

In vitro, capped RNAs have been reported to be translated more efficiently than uncapped transcripts in a variety of in vitro translation systems, such as rabbit reticulocyte lysate or wheat germ translation systems (see, e.g., Shimotohno, K., et al., PROC. NATL. ACAD. SCI. USA, 74:2734-2738 (1977); Paterson and Rosenberg, NATURE, 279:692 (1979)). This effect is also believed to be due in part to protection of the RNA from exoribonucleases present in the in vitro translation system, as well as other factors.

Naturally occurring cap structures comprise a 7-methyl guanosine that is linked via a triphosphate bridge to the 5'-end of the first transcribed nucleotide, resulting in a dinucleotide cap of $m^7G(5')ppp(5')N$, where N is any nucleoside. In vivo, the cap is added enzymatically. The cap is added in the nucleus and is catalyzed by the enzyme guanylyl transferase. The addition of the cap to the 5' terminal end of RNA occurs immediately after initiation of transcription. The terminal nucleoside is typically a guanosine, and is in the reverse orientation to all the other nucleotides, i.e., G(5')ppp(5')GpNpNp.

A common cap for mRNA produced by in vitro transcription is $m^7G(5')ppp(5')G$, which has been used as the dinucleotide cap in transcription with T7 or SP6 RNA polymerase in vitro to obtain RNAs having a cap structure in their 5'-termini. The prevailing method for the in vitro synthesis of capped mRNA employs a pre-formed dinucleotide of the form $m^7G(5')ppp(5')G$ ("$m^7GpppG$") as an initiator of transcription. A disadvantage of using $m^7G(5')ppp(5')G$, a pseudosymmetrical dinucleotide, is the propensity of the 3'-OH of either the G or $m^7G$ moiety to serve as the initiating nucleophile for transcriptional elongation. In other words, the presence of a 3'-OH on both the $m^7G$ and G moieties leads to up to half of the mRNAs incorporating caps in an improper orientation. This leads to the synthesis of two isomeric RNAs of the form $m^7G(5')pppG(pN)_n$ and $G(5')pppm^7G(pN)n$, in approximately equal proportions, depending upon the ionic conditions of the transcription reaction. Variations in the isomeric forms can adversely effect in vitro translation and are undesirable for a homogenous therapeutic product.

To date, the usual form of a synthetic dinucleotide cap used in in vitro translation experiments is the Anti-Reverse Cap Analog ("ARCA"), which is generally a modified cap analog in which the 2' or 3' OH group is replaced with $—OCH_3$. ARCA and triple-methylated cap analogs are incorporated in the forward orientation. Chemical modification of $m^7G$ at either the 2' or 3' OH group of the ribose ring results in the cap being incorporated solely in the forward orientation, even though the 2' OH group does not participate in the phosphodiester bond. (Jemielity, J. et al., "*Novel 'anti-reverse' cap analogs with superior translational properties*", RNA, 9:1108-1122 (2003)). The selective procedure for methylation of guanosine at N7 and 3' O-methylation and 5' diphosphate synthesis has been established (Kore, A. and Parmar, G. NUCLEOSIDES, NUCLEOTIDES, AND NUCLEIC ACIDS, 25:337-340, (2006) and Kore, A. R., et al. NUCLEOSIDES, NUCLEOTIDES, AND NUCLEIC ACIDS 25(3):307-14, (2006).

Transcription of RNA usually starts with a nucleoside triphosphate (usually a purine, A or G). In vitro transcription typically comprises a phage RNA polymerase such as T7, T3 or SP6, a DNA template containing a phage polymerase promoter, nucleotides (ATP, GTP, CTP and UTP) and a buffer containing magnesium salt. The synthesis of capped RNA includes the incorporation of a cap analog (e.g., $m^7GpppG$) in the transcription reaction, which in some embodiments is incorporated by the addition of recombinant guanylyl transferase. Excess $m^7GpppG$ to GTP (4:1) increases the opportunity that each transcript will have a 5' cap. Kits for capping of in vitro transcribed mRNAs are commercially available, including the mMESSAGE mMACHINE® kit (Ambion, Inc., Austin, Tex.). These kits will typically yield 80% capped RNA to 20% uncapped RNA, although total RNA yields are lower as GTP concentration becomes rate limiting as GTP is needed for the elongation of the transcript. However, currently there is no technology/method available that will allow quantification of capping efficiency without permanent alterations of the mRNAs in a sample.

Methods of estimating capping efficiency are known in the art. For example, the T7 RNA polymerase can be incubated with a cap dinucleotide, all four ribonucleotide triphosphates, $[\alpha-^{32}P]$ GTP, and a short DNA template in which G is the first ribonucleotide specified after the promoter (see Grudzien, E. et al. "*Novel cap analogs for in vitro synthesis of mRNA with high translation efficiency*", RNA, 10:1479-1487 (2004)). Any nucleotide on the 5' side of a G residue acquires a $^{32}P$-labeled 3'-phosphate group after RNase T2 digestion by nearest-neighbor transfer. Anion exchange chromatography is then used to resolve labeled nucleoside 3'-monophosphates, resulting from internal positions in the RNA, from 5'-terminal products. 5'-terminal products are of two types. Uncapped RNAs yield labeled guanosine 5'-triphosphate 3'-monophosphate (p3Gp*; in which * indicates the labeled phosphate group). Capped RNAs yield various 5'-terminal structures, depending on the nature of the cap analog used ($m^7Gp3Gp*$ and $Gp3m^7Gp*$ when the cap analog is $m^7Gp3G$).

However, a major drawback of these methods is that the entire sample is rendered radioactive or otherwise destroyed, and thus cannot be used in subsequent therapeutic applications. Although in theory a separate quantification reaction could be run alongside a therapeutic synthesis reaction, such arrangements are inadequate. Simultaneous but separate samples are inherently variable due to intra-operator error and minute variations in reaction conditions. This is particularly true for quantifications using a standard curve, in which a value for a point on the standard curve on one given day may not be the same on the next day. To obtain accurate results in calculating capping efficiency, it is desirable to use a representative sample taken from the therapeutic synthesis reaction, a sample for which capping efficiency can be evaluated relative to controls and which is representative of the capping efficiency in the therapeutic synthesis reaction.

Thus, the present invention provides improved methods of directly quantitating mRNA capping efficiency in a sample (e.g., a representative aliquot sample from an in vitro synthesis reaction). Some embodiments of the invention comprise the use of a cap specific binding substance under conditions that permit the formation of a complex between the cap specific binding substance and the capped mRNA. The formation of a complex between the cap specific binding substance and the capped mRNA allows quantitative determination of the amount of the complex (i.e., capped mRNAs) relative to a positive control of capped products or negative control of uncapped products. In other words, binding indicates the amount of capped mRNA targets in the sample and the capping efficiency in a reaction from which the sample is derived. Thus, in some embodiments, the step of quantitatively determining the amount of the complex comprises performing an ELISA-type assay wherein the cap specific binding substance is an antibody or other protein that specifically binds an mRNA cap. (see FIG. 1) Complex formation can be quantified by addition of a detection agent specific for the cap specific binding substance (e.g., a goat anti-mouse antibody that binds a mouse anti-$m^7G$ antibody) and which produces a signal directly proportional to the amount of capped mRNA. Embodiments of the invention may be used to quantify the capping efficiency of a wide variety of RNA species, including in vitro transcribed mRNA, isolated eukaryotic mRNA, and viral RNA. Embodiments of the invention can be used to quantify any of the cap structure and cap analogs described herein.

Inventive methods described herein are generally amenable to quantification of any type of mRNA cap. In some embodiments, the cap has a structure of formula I:

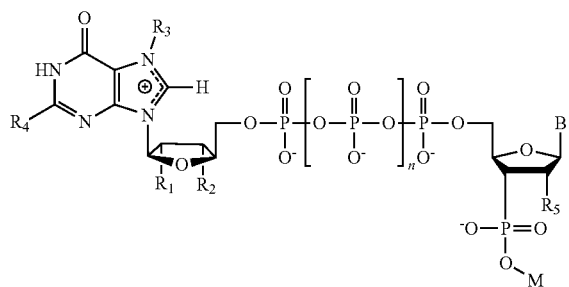

(I)

wherein B is a nucleobase, $R_1$ is selected from a halogen, OH, and $OCH_3$, $R_2$ is selected from H, OH, and $OCH_3$, $R_3$ is $CH_3$, $CH_2CH_3$, $CH_2CH_2CH_3$ or void, $R_4$ is $NH_2$, $R_5$ is selected from OH, $OCH_3$ and a halogen, n is 1, 2, or 3, and M is a nucleotide, i.e., the third base of mRNA. In particular embodiments, B is guanine, but can be any nucleobase. In some embodiments, the cap is $m^7G(5')ppp(5')G$ in which a 2'-O-methyl residue is present at the 2' OH group of the ribose ring of base 1 (i.e., at the $R_5$ position of Formula I).

In some embodiments, the cap has a structure of formula II:

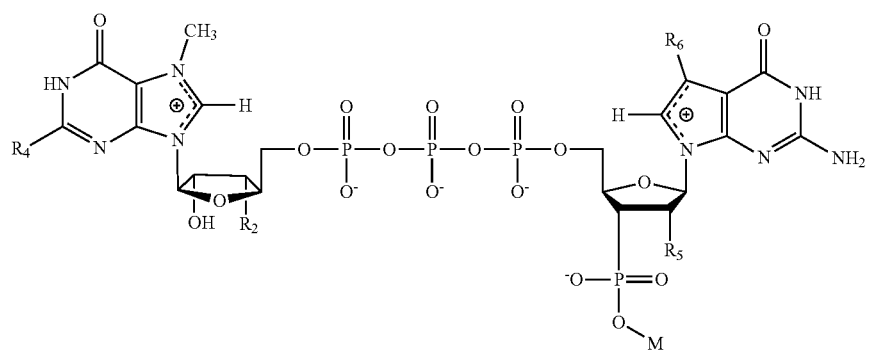

(II)

wherein $R_2$ is H or $CH_3$, $R_4$ is $NH_2$, $R_5$ is OH or $OCH_3$, $R_6$ is H or $CH_3$, and M is a nucleotide of the mRNA.

Cap analogs include, but are not limited to, a chemical structures selected from the group consisting of $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{7,2'd}GpppG$, $m^{7,3'Ome}GpppG$, $m^{7,3'd}GpppG$ and their tetraphosphate derivatives) (see, e.g., Jemielity, J. et al., "Novel 'anti-reverse' cap analogs with superior translational properties", RNA, 9:1108-1122 (2003)).

In a preferred embodiment, the cap is a 7-methyl guanylate ("$m^7G$") linked via a triphosphate bridge to the 5'-end of the first transcribed nucleotide, resulting in $m^7G(5')ppp(5')N$, where N is any nucleoside. A preferred embodiment of a $m^7G$ cap utilized in embodiments of the invention is $m^7G(5')ppp(5')G$.

Figure 2:
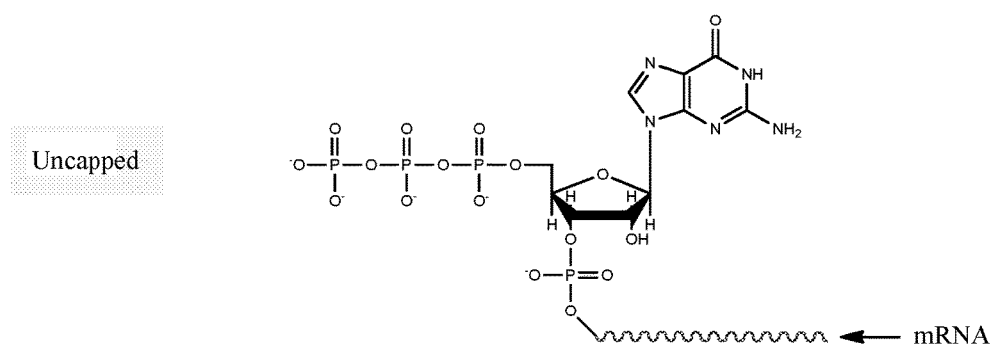
FIG. 2 is a diagram of exemplary mRNA capped structures and an uncapped structure present in various embodiments of the invention.
Figure 2:
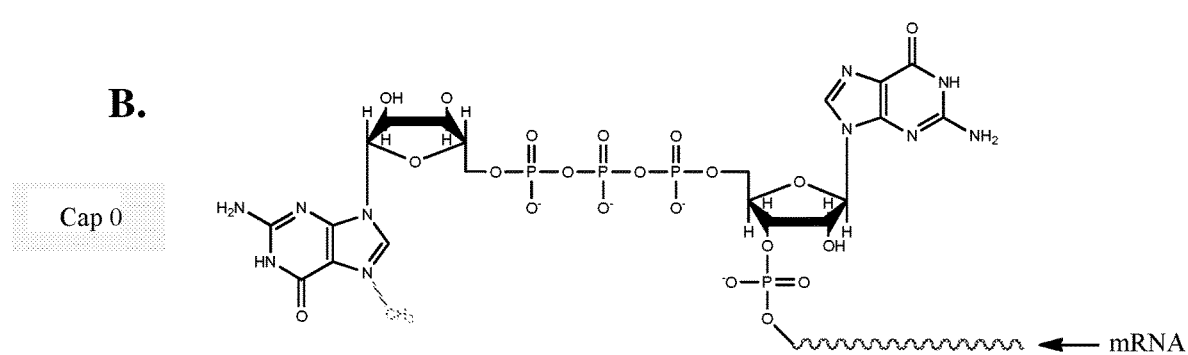
Figure 2:
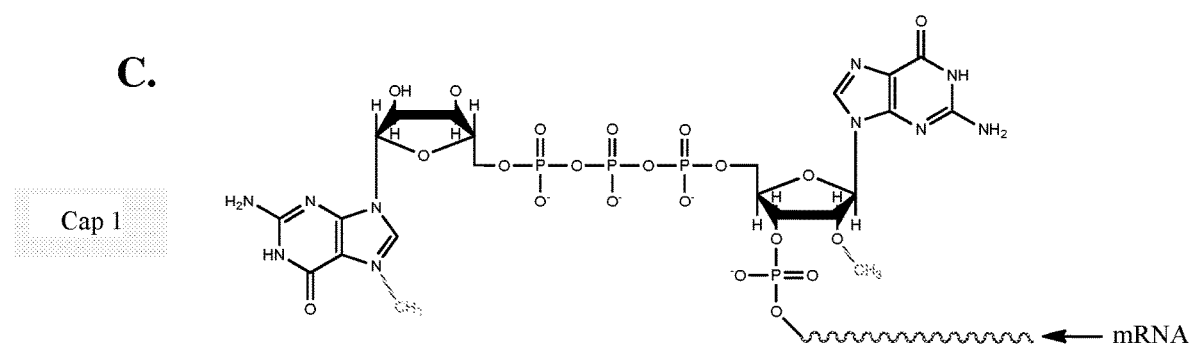

In some embodiments, mRNA is uncapped. (FIG. 2A) Uncapped mRNA may be present in a sample (i.e., as a result of incomplete capping in an in vitro transcription reaction) and/or may be used a control to quantitative the level of uncapped species in a sample. In some embodiments, the cap is a Cap0 structure. (FIG. 2B). Cap0 structures lack a 2'-O-methyl residue of the ribose attached to bases 1 and 2. In some embodiments, the cap is a Cap1 structure. (FIG. 2C) Cap1 structures have a 2'-O-methyl residue at base 1. In some embodiments, the cap is a Cap2 structure. Cap2 structures have a 2'-O-methyl residue attached to both bases 1 and 2.

A variety of $m^7G$ cap analogs are known in the art, many of which are commercially available. These include the $m^7GpppG$ described above, as well as the ARCA 3'-$OCH_3$ and 2'-$OCH_3$ cap analogs (Jemielity, J. et al., RNA, 9:1108-1122 (2003)). Additional cap analogs for use in embodiments of the invention include N7-benzylated dinucleoside tetraphosphate analogs (described in Grudzien, E. et al., RNA, 10:1479-1487 (2004)), phosphorothioate cap analogs (described in Grudzien-Nogalska, E., et al., RNA, 13:1745-1755 (2007)), and cap analogs (including biotinylated cap analogs) described in U.S. Pat. Nos. 8,093,367 and 8,304,529, incorporated by reference herein.

Production of Capped mRNAs

Capped mRNAs suitable for the quantitative methods disclosed herein may be produced by any method known in the art.

In some embodiments, capped mRNA is produced by in vitro transcription, originally developed by Krieg and Melton (METHODS ENZYMOL., 1987, 155:397-415) for the synthesis of RNA using an RNA phage polymerase. Typically these reactions include at least a phage RNA polymerase (T7, T3 or SP6), a DNA template containing a phage polymerase promoter, nucleotides (ATP, CTP, GTP and UTP), and a buffer containing a magnesium salt. RNA synthesis yields may be optimized by increasing nucleotide concentrations, adjusting magnesium concentrations and by including inorganic pyrophosphatase (U.S. Pat. No. 5,256,555; Gurevich, et al., ANAL. BIOCHEM. 195:207-213 (1991); Sampson, J. R. and Uhlenbeck, O. C., PROC. NATL. ACAD. SCI. USA. 85, 1033-1037 (1988); Wyatt, J. R., et al., BIOTECHNIQUES, 11:764-769 (1991)). Some embodiments utilize commercial kits for the large-scale synthesis of in vitro transcripts (e.g., MEGAscript®, Ambion). The RNA synthesized in these reactions is usually characterized by a 5' terminal nucleotide that has a triphosphate at the 5' position of the ribose. Typically, depending on the RNA polymerase and promoter combination used, this nucleotide is a guanosine, although it can be an adenosine (see e.g., Coleman, T. M., et al., NUCLEIC ACIDS RES., 32: e14 (2004)). In these reactions, all four nucleotides are typically included at equimolar concentrations and none of them is limiting.

Some embodiment of the invention are batch reactions—that is, all components are combined and then incubated at about 37° C. to promote the polymerization of the RNA until the reaction terminates. Typically, a batch reaction is used for convenience and to obtain as much RNA as needed from such reactions for their experiments. In some embodiments, a "fed-batch" system (see, e.g., JEFFREY A. KERN, BATCH AND FED-BATCH STRATEGIES FOR LARGE-SCALE PRODUCTION OF RNA BY IN VITRO TRANSACTION (University of Colorado) (1997)) is used to increase the efficiency of the in vitro transcription reaction. All components are combined, but then additional amounts of some of the reagents are added over time, such as the nucleotides and magnesium, to try to maintain constant reaction conditions. In addition, in some embodiments, the pH of the reaction may be held at 7.4 by monitoring it over time and adding KOH as needed.

To synthesize a capped RNA by in vitro transcription, a cap analog (e.g., N-7 methyl GpppG; i.e., m$^7$GpppG) is included in the transcription reaction. In some embodiments, the RNA polymerase will incorporate the cap analog as readily as any of the other nucleotides; that is, there is no bias for the cap analog. In some embodiments, the cap analog will be incorporated at the 5' terminus by the enzyme guanylyl transferase. In some embodiments, the cap analog will be incorporated only at the 5' terminus because it does not have a 5' triphosphate. In some embodiments using a T7, T3 and SP6 RNA polymerase, the +1 nucleotide of their respective promoters is usually a G residue and if both GTP and m$^7$GpppG are present in equal concentrations in the transcription reaction, then they each have an equal chance of being incorporated at the +1 position. In some embodiments, m$^7$GpppG is present in these reactions at several-fold higher concentrations than the GTP to increase the chances that a transcript will have a 5' cap. In some embodiments, a mMESSAGE mMACHINE® kit (Cat. #1344, Ambion, Inc.) is used according to manufacturer's instructions, where it is recommended that the cap to GTP ratio be 4:1 (6 mM:1.5 mM). In some embodiments, as the ratio of the cap analog to GTP increases in the reaction, the ratio of capped to uncapped RNA increases proportionally. Considerations of capping efficiency must be balanced with considerations of yield. Increasing the ratio of cap analog to GTP in the transcription reaction produces lower yields of total RNA because the concentration of GTP becomes limiting when holding the total concentration of cap and GTP constant. Thus, the final RNA yield is dependent on GTP concentration, which is necessary for the elongation of the transcript. The other nucleotides (ATP, CTP, UTP) are present in excess.

In particular embodiments, mRNA are synthesized by in vitro transcription from a plasmid DNA template encoding a gene of choice. In some embodiments, in vitro transcription includes addition of a 5' cap structure, Cap1 (FIG. 2C), which has a 2'-O-methyl residue at the 2' OH group of the ribose ring of base 1, by enzymatic conjugation of GTP via guanylyl transferase. In some embodiments, in vitro transcription includes addition of a 5' cap structure, Cap0 (FIG. 2B), which lacks the 2'-O-methyl residue, by enzymatic conjugation of GTP via guanylyl transferase. In some embodiments, in vitro transcription includes addition of a 5' cap of any of the cap structures disclosed herein by enzymatic conjugation of GTP via guanylyl transferase. In some embodiments, a 3' poly(A) tail of approximately 200 nucleotides in length (as determined by gel electrophoresis) was incorporated through the addition of ATP in conjunction with PolyA polymerase. In some embodiments, the poly(A) tail is approximately 100-250 nucleotides in length. In some embodiments, the poly(A) tail is about 50-300 nucleotides in length. In some embodiments, the in vitro transcription products include 5' and 3' untranslated regions.

Solid Substrates for Capturing mRNA

In some embodiments, capped mRNA is captured on a solid substrate before being contacted with a cap specific binding substance. These embodiments are not limited by the type of solid substrate. The only requirement of such embodiments is that the solid substrate must be able to directly or indirectly bind the capped mRNAs, and in some embodiments also uncapped mRNAs. The substrate may be a microplate, magnetic bead, particle, polymeric bead, chromatographic resin, filter paper, nitrocellulose, diazocellulose, glass, latex, polystyrene, polyvinylchloride, propylene, polyethylene, dextran, Sepharose, agar, starch, nylon, silica gel, or hydrogel.

In some embodiments, the solid support comprises a first capture agent that binds to mRNA that is capped or uncapped. In some embodiments, the first capture agent is a single-stranded polynucleotide sequence that corresponds to (i.e., is complementary with) a sequence in the single-stranded mRNA. Thus, when bound to a solid support, the polynucleotide first capture agent can hybridize with the mRNA. In a particular example, the first capture agent is a polythymidine tract (e.g., oligo-dT) that is capable of hybridizing to the poly A tail of mRNA. In some embodiments, a region of the 3' untranslated may be targeted by a first capture agent (e.g., an oligonucleotide of complementary sequence). In some embodiments, gene-specific coding regions of the mRNA may be targeted. The capture oligonucleotide can be about 10-50 nucleotides in length, e.g. about 10 nucleotides, about 15, nucleotides, about 20 nucleotides, about 25 nucleotides, about 30 nucleotides, or more.

A wide variety of nucleic acid sequences may be bound to a solid support in order to facilitate capture. Likewise, the manner in which polynucleotide capture agents are directly or indirectly attached to the solid support should not be limiting in any way. For example, in some embodiments, the polynucleotide capture agent can be synthesized on the surface in a manner suitable for deprotection but not cleavage from the synthesis support (see, e.g., Weiler et al., NUCL. ACIDS RES., 25(14):2792-2799 (1997)). In some embodiments, the polynucleotide capture agent can be covalently linked to a surface by the reaction of a suitable functional group on the isolation features with a functional group of the surface (see, e.g., Geiger et al., NUCLEOSIDES & NUCLEOTIDES 17(9-11):1717-1724 (1998)).

In a particular embodiments, the polythymidine tract oligonucleotide is biotinylated, and is thereby able to bind an avidin- or streptavidin-coated solid support. Biotinylated polythymidine tract oligonucleotides are commercially available (e.g., Promega, Invitrogen). Alternatively, polythymidine tract oligonucleotides or any other polynucleotide capture agent can be custom synthesized and biotinylated according to methods known to those of skill in the art. For example, biotin-11-dUTP residues may be added enzymatically, using terminal deoxynucleotidyl transferase, to the 3' terminus of a synthetic oligonucleotide (see, e.g., Riley, L. K. et al., DNA, 5:333-337 (1986)). A wide variety of avidin- and streptavidin-coated solid supports are also commercially available (e.g., Pierce 96-well streptavidin-coated microplates; Thermo Scientific).

Oligonucleotides may be synthesized by conventional means, e.g. via phosphoramidite chemistry on a commercial DNA synthesizer. In some embodiments, oligonucleotides are synthesized on a solid phase support as described by Gryaznov and Letsinger, NUCLEIC ACIDS RESEARCH, 20:3403-3409 (1992). Briefly, after deprotection, the 5' hydroxyl of a deoxythymidine linked to a support via a standard succinyl linkage is phosphitylated by reaction with chloro-(diisopropylethylamino)-methoxyphosphine in an appropriate solvent, such as dichloromethane/diisopropylethylamine. After activation with tetrazole, the 5'-phosphitylated thymidine is reacted with a 5'-trityl-O-3'-amino-3'-deoxynucleoside to form a nucleoside-thymidine dimer wherein the nucleoside moieties are covalently joined by a phosphoramidate linkage. The remainder of the oligonucleotide is synthesized by standard phosphoramidite chemistry. After cleaving the succinyl linkage, the oligonucleotide with a 3' terminal amino group is generated by cleaving the phosphoramidate link by acid treatment, e.g. 80% aqueous acetic acid for 18-20 hours at room temperature.

In some embodiments, the first capture agent is a protein. Any protein that selectively binds mRNA may be used. In some embodiments, a first capture agent protein binds the 3' end of the mRNA (e.g., poly(A) binding proteins). In other embodiments, first capture agent proteins bind to the 5' end of the mRNA (e.g., anti-m$^7$G antibodies). Exemplary proteins that can function as first capture agents include, poly (A) binding proteins ("PABP"), anti-m$^7$G antibodies and antigen-binding fragments thereof, and eukaryotic initiation factor 4E (eIF-4E). Methods of cap-dependent mRNA cap-dependent capture have been described previously (Edery, I. et al., MOL CELL BIOL, 15:3363-3371 (1995)); U.S. pre-grant publication 2007/0281336) and may be adapted to embodiments of the invention.

Methods for the chemical attachment of first capture agents (whether proteins or nucleic acids) to solid support surfaces can involve the reaction of a nucleophilic group, (e.g., an amine or thiol) of the capture agent to be immobilized, with an electrophilic group on the solid support surface. Alternatively, the nucleophile can be present on the support and the electrophile (e.g., activated carboxylic acid) can be present on the anti-isolation features. In some embodiments, first capture agents may be attached to a solid support by click chemistry. In some embodiments, first capture agents are attached via a 1,3-cycloaddition of an azide with an alkyne, optionally in the presence of a copper catalyst. Methods of using click chemistry are known in the art and include those described by Rostovtsev et al., Angew. CHEM. INT. ED. 41:2596-99 (2002) and Sun et al., BIOCONJUGATE CHEM., 17:52-57 (2006).

In some embodiments of the invention, first capture agents are directly attached to solid substrates via standard N-ethyl-N'-(dimethylaminopropyl) carbodiimide/N-hydroxysuccinimide (EDC/NHS) amine coupling procedures. Amine coupling introduces N-hydroxysuccinimide esters into the surface matrix by modification of the carboxymethyl groups with a mixture of N-hydroxysuccinimide (NHS) and N-ethyl-N'-(dimethylaminopropyl)-carbodiimide (EDC). These esters then react spontaneously with amines and other nucleophilic groups on the capture moiety to form covalent links. This is a highly stable and common surface functionalization technique. In some embodiments, first capture agents are bound directly to the solid substrate using a coating buffer of 50 mM NaHCO$_3$, pH 9.6.

Numerous types of solid supports derivatized with amino groups, carboxylic acid groups, isocyantes, isothiocyanates and malimide groups are commercially available, which can facilitate coupling of the first capture agent to the substrate.

In some embodiments where the first capture agents are proteins, the proteins may be biotinylated according to known methods, and subsequently bound to avidin- or streptavidin-coated solid substrates. Labeling reagents and kits are commercially available to specifically biotinylated antibodies and other proteins or peptides with biotin labels at primary amines (lysine and N-terminus), the most abundant reactive group on the surface of proteins, for streptavidin detection. For example, streptavidin-coated ELISA microplates may be coated with biotinylated polyA binding protein interacting protein (PAIP2). In some embodiments, commercially available human recombinant PAIP2 is biotinylated by amine-modified biotin labels to specifically biotinylate the C-terminus using the carbodiimide crosslinker EDC (EDAC).

In some embodiments, the first capture agents are tagged or otherwise modified to facilitate binding to the substrate. For example, in embodiments where the first capture agent is a protein (e.g, PABP), the protein may be produced recombinantly and tagged. For example, in some embodiments, first capture agent proteins are tagged with Glutathione S-transferase (GST). In some embodiments, the first capture agents are FLAG-tagged, HA-tagged, His-tagged or myc-tagged.

In certain embodiments, it is not necessary to use a first capture agent. As referenced above, embodiments of the invention include the incorporation of biotinylated cap analogs into samples of in vitro synthesized mRNAs to be quantitated. See, e.g., U.S. Pat. No. 8,344,118, to Kore et al., incorporated by reference herein. Biotinylated capped mRNA samples can be directly bound to avidin or streptavidin coated solid substrates.

In some embodiments, a second capture agent is bound directly to a solid substrate, which in turns binds the first capture agent. In some embodiments, the second capture agent is streptavidin or avidin, which can bind a biotinylated first capture agent (e.g. a biotinylated poly(A) binding protein). In some embodiments, the second capture agent is Protein A or Protein G. In some embodiments, the second capture agent is glutathione. In some embodiments, the second capture agent is a nickel-coated substrate, e.g., Ni Sepharose, NTA-agarose, His60 Ni, HisPur resin, or TALON resin. In some embodiments, the second capture agent is an antibody specific to the first capture agent; e.g., an anti-HA or anti-myc antibody.

It will be appreciated that the elegance of the methods described herein lies, in part, in their adaptability. All configurations of the arrangements described above are contemplated by the present disclosure. For example, in some embodiments, an mRNA is captured by its 3' end (e.g., by hybridization of immobilized oligo-dT or poly A-binding protein to the polyA tail), and the presence of a cap is quantified by formation of a complex between a cap specific binding substance and the capped mRNA. In other embodiments, however, it is possible to capture capped mRNA by its 5' end; e.g. by formation of a complex between the capped mRNA and a cap specific binding substance immobilized on a solid support, or if the cap is biotinylated by interaction with a streptavidin-coated plate). The presence of capped mRNA can then be quantified by addition of first detection agent that directly binds to an exposed polyA tail (i.e, a polyA-binding protein can function as a detection agent rather than a capture agent). Binding of the first capture agent to the polyA-tail can be visualized by addition of a second capture agent that generates a detectable signal (e.g., a HRP-conjugated anti-PABP antibody).

Cap Specific Binding Substance

A "cap specific binding substance", as used herein, references to any substance (protein, small molecule, etc.) that selectively binds to mRNA caps or cap analogs as described above. It is desirable that a cap specific binding substance suitable for the invention specifically or selectively binds to an mRNA cap or cap analog (e.g. those described herein), and that the binding event is detectable.

In some embodiments, a cap specific binding substance is a protein. In particular embodiments, the protein is eukaryotic initiation factor 4E ("eIF-4E"). eIF-4E has been utilized in cap-based mRNA purification (see, e.g., Edery, I. et al., "An efficient strategy to isolate full-length cDNAs based on an mRNA cap retention procedure (CAPture)", MOL. CELL. BIOL., 15:3363-3371 (1995)), and its cap-specific binding properties are adaptable for use in the present invention.

In some embodiments, a cap specific binding substance is a cap specific antibody including, but not limited to, antibodies specifically binding to $m^7G$, $m^7GpppG$, $m^7GpppA$, $m^7GpppC$; unmethylated cap analogs (e.g., GpppG); dimethylated cap analog (e.g., $m^{2,7}GpppG$), trimethylated cap analog (e.g., $m^{2,2,7}GpppG$), dimethylated symmetrical cap analogs (e.g., $m^7Gpppm^7G$), or anti reverse cap analogs (e.g., ARCA; $m^{7,2'Ome}GpppG$, $m^{7,2'd}GpppG$, $m^{7,3'Ome}GpppG$, $m^{7,3'd}GpppG$ and their tetraphosphate derivatives). Cap specific antibodies may be generated using standard methods. Exemplary anti-$m^7G$ antibodies are described in detail below.

Other cap specific binding protein may be utilized in embodiments of the invention. These include nuclear cap-binding protein subunit 1, nuclear cap-binding protein subunit 2, nuclear cap-binding complex, etc.

In some embodiments, cap specific binding proteins are modified (e.g., biotinylated or tagged) to facilitate binding to a solid support. For example, cap binding assays based on GST-eIF-4E are known in the art (see, e.g., McKracken, S. et al., "5'-capping enzymes are targeted to pre-mRNA by binding to the phosphorylated carboxy-terminal domain of RNA polymerase II", Genes & Dev., 11:3306-3318 (1997)).

As mentioned above, quantitative determination of the amount of the complex between the cap specific binding substance and the capped mRNA comprises measuring a detectable signal associated with formation of the complex. In some embodiments, the detectable signal is directly associated with the cap specific binding substance. In some embodiments, wherein the detectable signal is indirectly associated with the cap specific binding substance via a secondary agent that binds the cap specific binding substance (see, e.g., the ELISA discussion below, wherein the secondary agent is an antibody against the cap specific binding substance). Regardless of whether the detectable signal is directly or indirectly associated with the cap specific binding substance, the detectable signal may be a fluorescent signal, a colorimetric signal or a radioactive signal. In general, the intensity of the signal is directly proportional to the approximate amount of capped mRNA targets in the sample. Signals may also be selected from the group consisting of phycoerythrin, alexa 532, streptavidin-phycoerythrin and streptavidin-Alexa 532. In some embodiments, the signal is detected by enzymatic activity (i.e., horseradish peroxidase or alkaline phosphatase), chemiluminescence, radioactivity, infra-red emission, fluorescence resonance energy transfer (FRET) or any other method known to one of ordinary skill in the art.

Anti-$m^7G$ Cap Antibodies

In some embodiments, a cap specific binding protein is an anti-$m^7G$ antibody. Anti-$m^7G$ antibodies are known in the art and are commercially available. Anti-$m^7G$ antibodies for use in embodiments of the invention include those described in Meredith, R. D. and Erlanger, B. F., "Isolation and characterization of rabbit anti-$m^7G$-5'P antibodies of high apparent affinity", NUCLEIC ACIDS RES., 6:2179-2191 (1979), incorporated by reference herein. In particular embodiments, the antibody is a mouse monoclonal anti-$m^7G$-cap antibody (e.g. commercially available from Synaptic Systems).

Additional antibodies against $m^7G$ cap and cap analogs are encompassed within the scope of the present invention and can be generated by methods well known to those of skill in the art. As used herein, anti-$m^7G$ antibodies include any antibodies or fragments thereof antibodies that bind specifically to any epitopes of mRNA $m^7G$ caps. As used herein, the term "antibodies" is intended to include immunoglobulins and fragments thereof which are specifically reactive to the designated protein or peptide, or fragments thereof. For example, the term "antibodies" includes intact monoclonal antibodies, polyclonal antibodies, single domain antibodies (e.g., shark single domain antibodies (e.g., IgNAR or fragments thereof)), and antibody fragments so long as they exhibit the desired biological activity. Suitable antibodies also include, but are not limited to, mouse antibodies, goat antibodies, rabbit antibodies, human antibodies, primatized antibodies, chimeric antibodies, bi-specific antibodies, humanized antibodies, conjugated antibodies (i.e., antibodies conjugated or fused to other proteins, radiolabels, cytotoxins), and antibody fragments.

As used herein, an "antibody fragment" includes a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules. The term "antibody fragment" also includes any synthetic or genetically engineered protein that acts like an antibody by binding to a specific antigen to form a complex. For example, antibody fragments include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Anti-$m^7G$ antibodies can be generated using methods well known in the art. For example, protocols for antibody production are described by Harlow and Lane, *Antibodies: A Laboratory Manual*, (1988). Typically, antibodies can be generated in mouse, rat, guinea pig, hamster, camel, llama, shark, or other appropriate host. Alternatively, antibodies may be made in chickens, producing IgY molecules (Schade et al., *ALTEX* 13(5):80-85 (1996)). In some embodiments, antibodies suitable for the present invention are subhuman primate antibodies. For example, general techniques for raising therapeutically useful antibodies in baboons may be found, for example, in Goldenberg et al., international patent publication No. WO 91/11465 (1991), and in Losman et al., INT. J. CANCER, 46:310 (1990). In some embodiments, monoclonal antibodies may be prepared using hybridoma methods (Milstein and Cuello, NATURE, 305:537-40 (1983))). In some embodiments, monoclonal antibodies may also be made by recombinant methods (see, e.g., U.S. Pat. No. 4,166,452).

Many of the difficulties associated with generating monoclonal antibodies by B-cell immortalization can be overcome by engineering and expressing antibody fragments in *E. coli*, using phage display. To ensure the recovery of high affinity monoclonal antibodies, a combinatorial immunoglobulin library must typically contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., NATURE BIOTECH., 14:309 314 (1996). An scFv library with a large repertoire can be constructed by isolating V-genes from non-immunized human donors using PCR primers corresponding to all known $V_H$, $V_k$ and $V_\lambda$ gene families. Following amplification, the $V_k$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the JH region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., BIOTECHNOLOGY, 13:255 260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., BR. J. CANCER, 78:181 188 (1998); Osbourn et al., IMMUNOTECHNOLOGY, 2:181 196 (1996).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY 2:106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166 179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137 185 (Wiley-Liss, Inc. 1995).

In some embodiments, antibodies suitable for the invention may include humanized or human antibodies. Humanized forms of non-human antibodies are chimeric Igs, Ig chains or fragments (such as Fv, Fab, Fab', F(ab')2 or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., NATURE, 332:323-7 (1988); Verhoeyen et al., SCIENCE, 239:1534-6, (1988)). Such "humanized" antibodies are chimeric Abs (U.S. Pat. No. 4,816,567), wherein substantially less than an intact human variable domain has been substituted by the corresponding sequence from a non-human species. In some embodiments, humanized antibodies are typically human antibodies in which some CDR residues and possibly some FR residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence.

The use of high affinity anti-m$^7$G antibodies is important for quantitative specificity. Thus, in some embodiments, an anti-m$^7$G antibody or fragment thereof suitable for the present invention has a binding affinity of or greater than approximately 500 nM, 100 nM, 10 nM, 1 nM, 500 pM, 100 pM, 50 pM, 10 pM, 1 pM, 500 fM, 400 fM, 300 fM, 200 fM, 100 fM, 50 fM, 10 fM, 1 fM. In some embodiments, an anti-m$^7$G antibody or fragment thereof suitable for the present invention has a binding affinity ranging between approximately 500 nM and 1 fM, between 500 nM and 10 fM, between 500 nM and 100 fM, between 500 nM and 1 pM, between 10 nM and 1 fM, between 10 nM and 100 fM, between 10 nM and 1 pM, between 1 nM and 1 fM, between 1 nM and 100 fM, between 1 nM and 500 fM, between 1 nM and 1 pM, between 1 nM and 10 pM, between 1 nM and 50 pM, between 1 nM and 100 pM, between 1 nM and 500 pM.

ELISA-Based mRNA Cap Quantitation

Some embodiments of the invention entail an inventive method for the quantification of capping efficiency during messenger RNA (mRNA) synthesis comprising an ELISA-based assay using a first capture agent (e.g., a biotin-labeled poly-dT oligo) bound to a solid substrate (e.g. a streptavidin-coated 96-well plate or 384 well or other). The first capture agent is used to bind in vitro synthesized mRNA. Once bound, a cap specific binding substance is targeted to the m$^7$G cap moiety as its antigen. In some ELISA-based embodiments, the primary cap specific binding substance is an anti-m$^7$G antibody (e.g., a mouse monoclonal anti-m$^7$G antibody). A secondary labeled antibody is be used for visualization/quantitation (See FIG. 1). In some embodiments, the cap specific binding substance is another cap-specific protein (e.g., eIF-4E), and the secondary antibody is specific to the cap-specific protein. In some embodiments, the secondary antibody is or provides a detection agent; e.g., it possesses enzymatic activity to generate a detectable substrate. A variety of chromophoric/fluorescent agents can be substituted and applied. A custom synthesized biotinylated Cap (m⁷GpppG-Biotin) can be used as a positive control. This represents a new method for the direct quantification of capping moiety on a newly synthesized mRNA construct which is crucial to proper characterization. Protocols for ELISA assays and optimization of conditions are known in the art; see, e.g., Thermo Scientific, "Elisa technical guide and protocols", TECH TIP #65 (2010) (available at www.piercenet.com/files/TR0065-ELISA-guide.pdf), incorporated by reference herein.

Thus, in ELISA-based embodiments of the invention, the secondary agent is an antibody specific to the selective cap binding substance. In some embodiments, the secondary agent is radioactively or fluorescently labeled. In preferred embodiments, the secondary agent comprises an enzyme that converts a substrate to a detectable product. In some embodiments, the enzyme is alkaline phosphatase or horseradish peroxidase. The product may be chromogenic, chemifluorescent or chemiluminescent. In particular embodiments, the substrate is selected from the groups consisting of p-pitrophenyl phosphate disodium salt (PNPP), 2,2'-Azino-bis [3-ethylbenzothiazoline-6-sulfonic acid]-diammonium salt (ABTS), o-phenylenediamine dihydrochloride (OPD) or 3,3',5,5'-tetramethylbenzidine (TMB). In particular embodiments, the product is chromogenic and absorbs light at 370-652 nanometers. As described above, the intensity of signal is proportional to the approximate amount of capped RNA targets captured on the substrate.

Controls may be used to quantitate the amount of capped mRNA. In some embodiments, the control comprises an mRNA sample with a pre-determined amount of capped mRNA. In some embodiments, the control comprises a predetermined amount of synthesized cap. In some embodiments, a custom synthesized biotinylated Cap (m⁷GpppG-Biotin) is used as a positive control.

In some embodiments, assays are made quantitative by establishing a calibration curve by methods well known to those of skill in the art. In other words, the extent of the immunological reaction can be determined qualitatively or semi-quantitatively by visual comparison of the optical density of unknown samples with known standards or quantitatively by spectrophotometric comparison with standard curves prepared using a number of samples of known cap concentration. For example, quantitation may be performed by making a set of m⁷G cap standards or calibrators that retains the epitope of the primary antibody and can be bound by a solid substrate. These standards or calibrators can be serially diluted, and the resulting signal value from each tested concentration of standard or calibrator is used to generate a standard curve; plotting the concentration of capped standards or calibrators versus the resulting signal values. Once a standard quantitative curve is established, an assay is used to determine the levels of capped mRNA in a sample by plotting the resulting signal on the standard curve.

Kits

The present invention further provides kits comprising various reagents and materials useful for carrying out inventive methods according to the present invention. The quantitative procedures described herein may be performed by diagnostic laboratories, experimental laboratories, or commercial laboratories. The invention provides kits which can be used in these different settings.

For example, materials and reagents for quantifying mRNA capping efficiency in an mRNA sample by providing a cap specific binding substance according to the inventive methods may be assembled together in a kit. In certain embodiments, an inventive kit comprises at least one or more reagents that specifically form a complex with an mRNA cap, optionally agents for detecting formation of the complex, and instructions for using the kit according to a method of the invention.

Each kit may preferably comprise the reagent which renders the procedure specific. Thus, for detecting/quantifying mRNA capping efficiency, the reagent that specifically forms a complex with the cap may be an antibody. Kits may also comprise detection or secondary agents (e.g., HRP-conjugated antibodies) that detect formation of the complex. Kits may also comprise solid substrates, optionally conjugated with a second capture agent for isolation of mRNA (e.g., biotinylated 96-well plates). Kits may also comprise first capture agents, e.g., proteins or oligonucleotides that specifically interact with mRNA.

Kits or other articles of manufacture according to the invention may include one or more containers to hold various reagents. Suitable containers include, for example, bottles, vials, syringes (e.g., pre-filled syringes), ampules. The container may be formed from a variety of materials such as glass or plastic.

In some embodiments, kits of the present invention may include suitable control levels or control samples for determining control levels as described herein. In some embodiments, kits of the invention may include instructions for using the kit according to one or more methods of the invention and may comprise instructions for in vitro transcription and capping.

EXAMPLES

Example 1: Synthesis of mRNA

Firefly Luciferase (FFL) and human erythropoietin (EPO) mRNA were synthesized by in vitro transcription from a plasmid DNA template encoding each respective gene. In vitro transcription included addition of a 5' cap structure, Cap1, which has a 2'-O-methyl residue at the 2' OH group of the ribose ring of base 1, by enzymatic conjugation of GTP via guanylyl transferase. A 3' poly(A) tail of approximately 200 nucleotides in length (as determined by gel electrophoresis) was incorporated through the addition of ATP in conjunction with PolyA polymerase (see detailed reaction conditions below). The in vitro transcription product included 5' and 3' untranslated regions, which are represented as X and Y, respectively, in the sequences below:

Human Erythropoietin (EPO) mRNA
(SEQ ID NO: 1)
X₁AUGGGGGUGCACGAAUGUCCUGCCUGGCUGUGGCUUCUCCUGUCCCU

GCUGUCGCUCCCUCUGGGCCUCCCAGUCCUGGGCGCCCCACCACGCCUCA

UCUGUGACAGCCGAGUCCUGGAGAGGUACCUCUUGGAGGCCAAGGAGGC

CGAGAAUAUCACGACGGGCUGUGCUGAACACUGCAGCUUGAAUGAGAAU

AUCACUGUCCCAGACACCAAAGUUAAUUUCUAUGCCUGGAAGAGGAUGG

AGGUCGGGCAGCAGGCCGUAGAAGUCUGGCAGGGCCUGGCCCUGCUGUC

GGAAGCUGUCCUGCGGGGCCAGGCCCUGUUGGUCAACUCUUCCCAGCCG

UGGGAGCCCCUGCAGCUGCAUGUGGAUAAAGCCGUCAGUGGCCUUCGCA

GCCUCACCACUCUGCUUCGGGCUGUGGGAGCCCAGAAGGAAGCCAUCUC

CCCUCCAGAUGCGGCCUCAGCUGGUCCACUCCGAACAAUCACUGCUGAC

-continued

ACUUUCCGCAAACUCUUCCGAGUCUACUCCAAUUUCCUCCGGGGAAAGC

UGAAGCUGUACACAGGGGAGGCCUGGAGGACAGGGGACAGAUGA$Y_1$

Codon-Optimized Firefly Luciferase (FEL) mRNA
(SEQ ID NO: 2)
$X_2$AUGGAAGAUGCCAAAAACAUUAAGAAGGGCCCAGCGCCAUUCUACCC

ACUCGAAGACGGGACCGCCGGCGAGCAGCUGCACAAAGCCAUGAAGCGC

UACGMCUGGUGCCCGGCACCAUCGCCUUUACCGACGCACAUAUCGAGG

UGGACAUUACCUACGCCGAGUACUUCGAGAUGAGCGUUCGGCUGGCAGA

AGCUAUGAAGCGCUAUGGGCUGAAUACAAACCAUCGGAUCGUGGUGUGC

AGCGAGAAUAGCUUGCAGUUCUUCAUGCCCGUGUUGGGUGCCCUGUUCA

UCGGUGUGGCUGUGGCCCCAGCUAACGACAUCUACAACGAGCGCGAGCU

GCUGAACAGCAUGGGCAUCAGCCAGCCCACCGUCGUAUUCGUGAGCAAG

AAAGGGCUGCAAAAGAUCCUCAACGUGCAAAAGAAGCUACCGAUCAUAC

AAAAGAUCAUCAUCAUGGAUAGCAAGACCGACUACCAGGGCUUCCAAAG

CAUGUACACCUUCGUGACUUCCCAUUUGCCACCCGGCUUCAACGAGUAC

GACUUCGUGCCCGAGAGCUUCGACCGGGACAAAACCAUCGCCCUGAUCA

UGAACAGUAGUGGCAGUACCGGAUUGCCCAAGGGCGUAGCCCUACCGCA

CCGCACCGCUUGUGUCCGAUUCAGUCAUGCCCGCGACCCCAUCUUCQGC

AACCAGAUCAUCCCCGACACCGCUAUCCUCAGCGUGGUGCCAUUUCACC

ACGGCUUCGGCAUGUUCACCACGCUGGGCUACUUGAUCUGCGGCUUUCG

GGUCGUGCUCAUGUACCGCUUCGAGGAGGAGCUAUUCUUGCGCAGCUUG

CAAGACUAUAAGAUUCAAUCUGCCCUGCUGGUGCCCACACUAUUUAGCU

UCUUCGCUAAGAGCACUCUCAUCGACAAGUACGACCUAAGCAACUUGCA

CGAGAUCGCCAGCGGCGGGGCGCCGCUCAGCAAGGAGGUAGGUGAGGCC

GUGGCCAAACGCUUCCACCUACCAGGCGCAUCCGCCAGGGCUACGGCCUGA

CAGAAACAACCAGCGCCAUUCUGAUCACCCCCGAAGGGGACGACAAGCC

UGGCGCAGUAGGCAAGGUGGUGCCCUUCUUCGAGGCUAAGGUGGUGGAC

UUGGACACCGGUAAGACACUGGGUGUGAACCAGCGCGGCGAGCUGUGCG

UCCGUGGCCCCAUGAUCAUGAGCGGCUACGUUAACAACCCCGAGGCUAC

AAACGCUCUCAUCGACAAGGACGGCUGGCUGCACAGCGGCGACAUCGCC

UACUGGGACGAGGACGAGCACUUCUUCAUCGUGGACCGGCUGAAGAGCC

UGAUCAAAUACAAGGGCUACCAGGUAGCCCCAGCCGAACUGGAGAGCAU

CCUGCUGCAACACCCCAACAUCUUCGACGCCGGGGUCGCCGGCCUGCCCG

ACGACGAUGCCGGCGAGCUGCCCGCCGCAGUCGUCGUGCUGGAACACGG

UAAAACCAUGACCGAGAAGGAGAUCGUGGACUAUGUGGCCAGCCAGGUU

ACAACCGCCAAGAAGCUGCGCGGUGGUGUUGUGUUCGUGGACGAGGUGC

CUAAAGGACUGACCGGCAAGUUGGACGCCCGCAAGAUCCGCGAGAUUCU

CAUUAAGGCCAAGAAGGGCGGCAAGAUCGCCGUGUA$Y_2$

The 5' and 3' UTR sequences for X1/Y1 and X2/Y2 were as follows:

(SEQ ID NO: 3)
$X_1$ = GGACAGAUCGCCUGGAGACGCCAUCCACGCUGUUUUGACCUCCAU

AGAAGACACCGGGACCGAUCCAGCCUCCGCGGCCGGGAACGGUGCAUUGG

AACGCGGAUUCCCCGUGCCAAGAGUGACUCACCGUCCUUGACACG (SEQ ID NO: 4)
$X_2$ = GGGAUCCUACC (SEQ ID NO: 5)
$Y_1$ = CGGGUGGCAUCCCUGUGACCCCUCCCCAGUGCCUCUCCUGGCCCU

GGAAGUUGCCACUCCAGUGCCCACCAGCCUUGUCCUAAUAAAAUUAAGUU

GCAUC (SEQ ID NO: 6)
$Y_2$ = UUUGAAUU

The synthesis of mRNA was conducted under complete RNAse-free conditions. All tubes, vials, pipette tips, pipettes, buffers, etc. were required nuclease-free. Messenger RNA was synthesized from a linearized DNA template. To produce the desired mRNA pre-cursor (IVT) construct, a mixture of ~100 ug of linearized DNA, rNTPs (3.33 mM), DTT (10 mM), T7 RNA polymerase, RNAse Inhibitor, Pyrophosphatase and reaction buffer (10×, 800 mM Hepes (pH 8.0), 20 mM Spermidine, 250 mM $MgCl_2$, pH 7.7) was prepared with RNase-free water to a final volume of 2.24 ml. The reaction mixture was incubated at 37° C. for between 20-120 minutes. Upon completion, the mixture was treated with DNase I for an additional 15 minutes and quenched accordingly.

The purified mRNA product from the aforementioned IVT step was denatured at 65° C. for 10 minutes. Separately, portions of GTP (20 mM), S-adenosyl methionine, RNAse inhibitor, 2'-O-Methyltransferase and guanylyl transferase are mixed together with reaction buffer (10×, 500 mM Tris-HCl (pH 8.0), 60 mM KCl, 12.5 mM $MgCl_2$) to a final concentration of 8.3 ml. Upon denaturation, the mRNA was cooled on ice and then added to the reaction mixture. The combined solution was incubated at 37° C. for 20-90 minutes. Upon completion, aliquots of ATP (20 mM), PolyA Polymerase and tailing reaction buffer (10×, 500 mM Tris-HCl (pH 8.0), 2.5M NaCl, 100 mM $MgCl_2$) were added, and the total reaction mixture was further incubated at 37° C. for about 20-45 minutes. Upon completion, the final reaction mixture is quenched and purified accordingly.

Example 2: Quantification of Capping Efficiency Using Biotin-Streptavidin-Based Oligo-dT Capture ELISA This example illustrates an exemplary ELISA method to quantify capping efficiency. An exemplary embodiment is depicted in FIG. 1. A commercially available streptavidin microplate was washed 3 times with wash buffer (0.05% Tween 20, 0.01M PBS pH 7.2) and patted dry. Commercially available 5' biotin Oligo dT20 was added at 1-5 pmol/well in a final volume of 100 μl and incubated at room temperature (RT) for one hour. The plate was washed three times with wash buffer and blocked for 1 hr with 320 μl blocking buffer (0.01M PBS, 0.5% BSA, 0.15% Tween 20).

Messenger RNA samples were denatured for 10 minutes at 94° C. and incubated at RT for 30 minutes. 100 μl of hybridization buffer (4×SSC, 20 mM HEPES, 2 mM EDTA, 0.15% Tween 20) containing 20 pmol-1 μmol of mRNA was added to each well and incubated at RT for 1 hour. The plate was washed three times with wash buffer containing 2 mM EDTA A primary antibody, mouse monoclonal anti-m$^7$G cap (1:2000-1:25000 dilution in 100 μl aliquots) was applied to each well of the plate and incubated at RT for approximately 1 hour. The plate was washed three times with wash buffer containing 2 mM EDTA. After washing, 100 μl of a secondary antibody, goat anti-mouse HRP-conjugate antibody (1:40,000 dilution), was added to each well and incubated at RT for 1 hour. The plate was washed three times with wash buffer containing 2 mM EDTA.

To detect interaction of the primary and secondary antibodies, TMB (3,3',5,5'-tetramethylbenzidine) chromogenic substrate solution was prepared according to manufacturer's instructions, added to each well in 100 μl aliquots, and incubated for 15 min at RT. The reaction was stopped by adding 100 μL of 2N $H_2SO_4$.

The TMB produced a recognizably a blue color when detecting HRP. Following addition of the $H_2SO_4$, the color changed to yellow with maximum absorbance at 450 nm, which was read using a Molecular Devices plate reader.

It is found that a well with absorbance at 450 nm indicated the presence of a capped mRNA. Quantitative measurement of capped mRNA per sample is determined from mean absorbance values of the sample followed by interpolation of a standard curve (plotting concentration versus absorbance) generated from serially diluted positive controls of biotin-conjugated m$^7$G-cap small molecule bound to streptavidin coated plates and detected by mouse monoclonal m$^7$G-cap antibody (Synaptic systems).

Example 3: Quantification of Capping Efficiency Using PolyA Binding Protein-Based Capture ELISA This example illustrates another exemplary ELISA method using polyA binding protein coated ELISA plates. Specifically, an ELISA plate is coated with poly A-binding protein ("PABP") at 1 μg/ml using coating buffer (50 mM NaHCO3, pH 9.6). The plate is subsequently washed and blocked with blocking buffer (1×PBS, 0.05% Tween 20, 2% BSA), and incubated for one hour at room temperature. The plate is then washed three times with wash buffer (1×PBS, 0.05% Tween 20).

mRNA samples are denatured for 10 minutes at 94° C. and incubated at room temperature for 30 minutes. The samples are then diluted to a concentration of approximately (20 pmol-1 μmol) in hybridization buffer (4×SSC, 20 mM HEPES, 2 mM EDTA, 0.15% Tween 20) containing RNA. Approximately 100 μl is added to each well and incubated for one hour at RT.

A primary antibody, mouse monoclonal anti-m$^7$G cap (1:2000-1:25000 dilution in 100 μl aliquots) is applied to each well of the plate and incubated at RT for approximately 1 hour. The plate is washed three times with wash buffer containing 2 mM EDTA followed by addition of goat anti-mouse IgG Fc HRP-conjugated secondary antibody (Pierce 31439) at 1:40,000 dilution and incubation at RT for 1 hour. After washing 3× with wash buffer, TMB is prepared and added as above. After 15 min incubation at RT, the reaction was stopped by adding 2N $H_2SO_4$ and the plate read at 450 nm as above.

In alternative embodiments, commercially available microplates are used onto which antibody specific for PAIP2 has been pre-coated. 100 μl of commercially available human recombinant PAIP2 (Cusabio®) at 0.1 μg/ml-10 μg/ml is added per well using coating buffer (50 mM NaHCO$_3$, pH 9.6), followed by a one hour incubation at room temperature. Human recombinant PAIP2 present is bound by the immobilized antibody. After removing any unbound substances, mRNA samples are added to the wells as above for capping efficiency quantitation. A primary antibody, mouse monoclonal anti-m$^7$G cap (1:2000-1:25000 dilution in 100 μl aliquots) is applied to each well of the plate and incubated at RT for approximately 1 hour. The plate is washed three times with wash buffer containing 2 mM EDTA. After washing, 100 μl of a secondary antibody, goat anti-mouse HRP-conjugate antibody (1:40,000 dilution), is added to each well and incubated at RT for 1 hour. The plate is washed three times followed by addition of the TMB chromogenic substrate solution. The color development is stopped, the intensity of the color is measured and the amount of capped mRNA quantitated using a standard curve as above.

Example 4: Evaluation of mRNA 5' Capping on In Vivo Protein Production

In this example, we evaluated the impact of mRNA 5' capping on in vivo protein production and its potential impact on the efficacy of mRNA based therapy. Specifically, we evaluated the impact of 5' capping on the in vivo production of alpha-galactosidase A (alpha-Gal A), which is deficient in Fabry disease. Fabry disease is an X-linked inherited lysosomal storage disease characterized by severe renal impairment, angiokeratomas, and cardiovascular abnormalities, including ventricular enlargement and mitral valve insufficiency. Fabry disease also affects the peripheral nervous system, causing episodes of agonizing, burning pain in the extremities. Fabry disease is caused by a deficiency in the enzyme alpha-galactosidase A (alpha-Gal A). alpha-Gal A is the lysosomal glycohydrolase that cleaves the terminal alpha-galactosyl moieties of various glycoconjugates. Fabry disease results in a blockage of the catabolism of the neutral glycosphingolipid, ceramide trihexoside (CTH), and accumulation of this enzyme substrate within cells and in the bloodstream.

The cDNA and gene encoding human alpha-Gal A, GLA, have been isolated and sequenced. Human alpha-Gal A is expressed as a 429-amino acid polypeptide, of which the N-terminal 31 amino acids are the signal peptide. The human enzyme has been expressed in Chinese Hamster Ovary (CHO) cells (Desnick et al., U.S. Pat. No. 5,356,804; Ioannou et al., J. CELL BIOL. 119:1137 (1992)); and insect cells (Calhoun et al., WO 90/11353).

Individuals suffering from Fabry disease may be treated by enzyme replacement therapy with human alpha-Gal A (see, e.g., U.S. Pat. No. 6,458,574, incorporated by reference herein). Additional approaches that modulate or supplement the expression of alpha-Gal A deficiency, and thus ameliorate the underlying deficiency, would be useful in the development of appropriate therapies for associated disorders. Such approaches include methods of intracellular delivery of nucleic acids (e.g., GLA mRNA) that are capable of correcting existing genetic defects and/or providing beneficial functions to one or more target cells. Following successful delivery to target tissues and cells, the compositions and nucleic acids transfect the target cell, and the nucleic acids (e.g., GLA mRNA) can be translated into the gene product of interest (e.g., alpha-GAL A) or can otherwise modulate/regulate the presence or expression of the gene product of interest. Such methods have been described previously; see, e.g. U.S. pre-grant publication 2011/0244026, incorporated by reference herein.

In this example, we evaluated the impact of the 5' capping on the in vivo protein production. Human GLA mRNA was synthesized by in vitro transcription from a plasmid DNA template encoding the gene, which was followed by the addition of a 5' cap structure, either Cap0 or Cap1 (Fechter, P. et al., J. GEN. VIROLOGY, 86:1239-1249 (2005)). A 3' poly(A) tail of approximately 200 nucleotides in length as determined by gel electrophoresis was also added. The 5' and 3' untranslated regions present in the GLA mRNA are represented as X and Y in SEQ ID NO: 7, as indicated below:

Alpha-galactosidase (GLA) mRNA(SEQ ID NO: 7):
$X_2$AUGCAGCUGAGGAACCCAGAACUACAUGUGGGCUGCGCGCUUGCGCUU
CGCUUCCUGGCCCUCGUUUCCUGGGACAUCCCUGGGGCUAGAGCACUGGA
CAAUGGAUUGGCAAGGACGCCUACCAUGGGCUGGCUGCACUGGGAGCGCU
UCAUGUGCAACCUUGACUGCCAGGAAGAGCCAGAUUCCUGCAUGAGUGAG
AAGCUCUUCAUGGAGAUGGCAGAGCUCAUGGUCUCAGAAGGCUGGAAGGA
UGCAGGUUAUGAGUACCUCUGCAUUGAUGACUGUUGGAUGGCUCCCCAAA
GAGAUUCAGAAGGCAGACUUCAGGCAGACCCUCAGCGCUUUCCUCAUGGG
AUUCGCCAGCUAGCUAAUUAUGUUCACAGCAAAGGACUGAAGCUAGGGAU
UUAUGCAGAUGUUGGAAAUAAAACCUGCGCAGGCUUCCCUGGGAGUUUUG
GAUACUACGACAUUGAUGCCCAGACCUUUGCUGACUGUGGAGUAGAUCUG
CUAAAAUUUGAUGGUUGUUACUGUGACAGUUUGGAAAAUUUGGCAGAUGG
UUAUAAGCACAUGUCCUUGGCCCUGAAUAGGACUGGCAGAAGCAUUGUGU
ACUCCUGUGAGUGGCCUCUUUAUAUGUGGCCCUUUCAAAAGCCCAAUUAU
ACAGAAAUCCGACAGUACUGCAAUCACUGGCGAAAUUUUGCUGACAUUGA
UGAUUCCUGGAAAAGUAUAAAGAGUAUCUUGGACUGGAGAUCUUUUAACC
AGGAGAGAAUUGUUGAUGUUGCUGGACCAGGGGGUUGGAAUGACCCAGAU
AUGUUAGUGAUUGGCAACUUUGGCCUCAGCUGGAAUCAGCAAGUAACUCA
GAUGGCCCUCUGGGCUAUCAUGGCUGCUCCUUUAUUCAUGUCUAAUGACC
UCCGACACAUCAGCCCUCAAGCCAAAGCUCUCCUUCAGGAUAAGGACGUA
AUUGCCAUCAAUCAGGACCCCUUGGGCAAGCAAGGGUACCAGGUUAGACA
GGGAGACAACUUUGAAGUGUGGGAACGACCUCUCUCAGGCUUAGCCUGGG
CUGUAGCUAUGAUAAACCGGCAGGAGAUUGGUGGACCUCGCUCUUAUACC
AUCGCAGUUGCUUCCCUGGGUAAAGGAGUGGCCUGUAAUCCUGCCUGCUU
CAUCACACAGCUCCUCCCUGUGAAAAGGAAGCUAGGGUUCUAUGAAUGGA
CUUCAAGGUUAAGAAGUCACAUAAAUCCCACAGGCACUGUUUUGCUUCAG
CUAGAAAAUACAAUGCAGAUGUCAUUAAAAGACUUACUUUAA$Y_2$ (SEQ ID NO: 4)
X = GGGAUCCUACC (SEQ ID NO: 6)
Y = UUUGAAUU A codon-optimized alpha-galactosidase with PolyA insert (CO-GLA-PolyA) is also utilized in some embodiments (SEQ ID NO: 8):

$X_1$AUGCAGCUGAGGAACCCAGAGCUCCAUCUCGGAUGUGCACUGGCACUU
AGAUUUCUCGCGCUUGUGUCGUGGGACAUCCCCGGAGCCAGGGCGCUGGA
UAAUGGGCUCGCCCGGACUCCCACAAUGGGUUGGCUGCACUGGGAGCGCU
UUAUGUGCAAUCUGGACUGCCAGGAAGAGCCCGAUAGCUGUAUUUCGGAG
AAGCUCUUCAUGGAAAUGGCGGAGUUGAUGGUGUCCGAAGGGUGGAAGGA
UGCGGGAUAUGAGUAUCUGUGUAUCGAUGACUGCUGGAUGGCACCGCAGC
GAGAUUCGGAGGGGCGAUUGCAGGCCGACCCUCAGCGCUUCCCUCAUGGA
AUUCGGCAGCUGGCCAACUACGUACACUCAAAAGGACUUAAGUUGGGGAU
CUACGCGGACGUCGGUAAUAAGACAUGCGCUGGGUUCCCGGGGAGCUUCG
GAUACUAUGAUAUUGAUGCCCAGACCUUCGCGGACUGGGGAGUGGACUUG
CUUAAGUUUGAUGGUUGUUACUGUGACUCAUUGGAAAACUUGGCGGAUGG
GUAUAAACAUAUGUCCUUGGCCUUGAAUCGGACAGGGCGGUCGAUCGUCU
ACAGCUGCGAAUGGCCUUUGUAUAUGUGGCCGUUCCAGAAACCCAACUAC
ACCGAAAUUCGCCAGUAUUGCAAUCACUGGAGAAACUUCGCCGAUAUCGA
CGAUUCGUGGAAAUCAAUCAAGUCCAUCCUCGACUGGACGUCCUUCAACC
AAGAGAGAAUCGUAGAUGUGGCCGGACCGGGAGGAUGGAACGACCCUGAU
AUGCUUGUAAUUGGCAACUUUGGACUCUCGUGGAACCAGCAAGUAACGCA
AAUGGCACUCUGGGCUAUCAUGGCUGCGCCCCUGUUCAUGUCAAACGACC
UCAGGCACAUCUCGCCGCAGGCGAAAGCCUUGCUUCAAGAUAAGGACGUC
AUCGCGAUUAAUCAGGACCCGCUGGGGAAGCAGGGCUAUCAGCUUAGACA
GGGCGACAAUUUUGAGGUCUGGGAGCGACCCCUGAGCGGACUCGCAUGGG
CGGUGGCAAUGAUCAAUAGGCAGGAAAUUGGUGGGCCGAGGUCGUACACU
AUCGCCGUCGCGUCGUUGGGAAAGGGUGUGGCGUGUAAUCCAGCGUGCUU
UAUCACCCAACUGCUGCCCGUCAAGCGCAAACUGGGUUUUUACGAAUGGA
CGAGCAGACUUCGCUCACACAUUAACCCAACGGGUACGGUGUUGCUCCAG
CUCGAGAAUACAAUGCAAAUGUCACUUAAAGAUUUGCUCUGACGGGUGGC
AUCCCUGUGACCCCUCCCCAGUGCCUCUCCUGGCCCUGGAAGUUGCCACU
CCAGUGCCCACCAGCCUUGUCCUAAUAAAAUUAAGUUGCAUCAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAA

The GLA mRNA was stored in water at a final concentration of 1 mg/mL at −80° C. until the time of use. All mRNA concentrations were determined via absorption (γmax 260 nm).

Suitable formulations for in vivo delivery of GLA Cap0 mRNA, GLA Cap1 mRNA, GLA mRNA and other controls include a multi-component lipid mixture of varying ratios employing one or more cationic lipids, helper lipids and PEGylated lipids. Cationic lipids can include (but not exclusively) DOTAP (1,2-dioleyl-3-trimethylammonium propane), DODAP (1,2-dioleyl-3-dimethylammonium propane), DOTMA (1,2-di-O-octadecenyl-3-trimethylammonium propane), DLinDMA (Heyes, J.; Palmer, L.; Bremner, K.; MacLachlan, I., "Cationic lipid saturation influences intracellular delivery of encapsulated nucleic acids" J. CONTR. REL., 107:276-287 (2005)), DLin- KC2-DMA (Semple, S. C. et al. "Rational Design of Cationic Lipids for siRNA Delivery", NATURE BIOTECH., 28:172-176 (2010)), C12-200 (Love, K. T. et al. "Lipid-like materials for low-dose in vivo gene silencing", PROC NATL ACAD SCI. USA, 107:1864-1869 (2010)), HGT4003, ICE, dialkylamino-based, imidazole-based, guanidinium-based, etc. Helper lipids can include (but not exclusively) DSPC (1,2-distearoyl-sn-glycero-3-phosphocholine), DPPC (1,2-dipalmitoyl-sn-glycero-3-phosphocholine), DOPE (1,2-dioleyl-sn-glycero-3-phosphoethanolamine), DPPE (1,2-dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)), cholesterol, etc. The PEGylated lipids can include (but not exclusively) a poly(ethylene) glycol chain of up to 5 kDa in length covalently attached to a lipid with alkyl chain(s) of C6-C20 length. Lipid encapsulation of mRNA was calculated by performing the Ribogreen assay with and without the presence of 0.1% Triton-X 100. Particle sizes (dynamic light scattering (DLS)) and zeta potentials were determined using a Malvern Zetasizer instrument in 1×PBS and 1 mM KCl solutions, respectively.

Aliquots of 50 mg/mL ethanolic solutions of C12-200, DOPE, Chol and DMG-PEG2K were mixed and diluted with ethanol to 3 mL final volume. Separately, an aqueous buffered solution (10 mM citrate/150 mM NaCl, pH 4.5) of CO-GLA mRNA (Cap 0 or Cap 1) was prepared from a 1 mg/mL stock. The lipid solution was injected rapidly into the aqueous mRNA solution and shaken to yield a final suspension in 20% ethanol. The resulting nanoparticle suspension was filtered, diafiltrated with 1×PBS (pH 7.4), concentrated and stored at 2-8° C. Final concentration=0.72 mg/mL GLA mRNA (encapsulated). Zave=85.5 nm (Dv(50)=61.9 nm; Dv(90)=113 nm).

To determine whether the type of cap incorporated into GLA mRNA influenced protein production when the mRNA was encapsulated into C12-200-based lipid, an experiment was conducted in which wild type (CD-1) mice were injected with capped GLA mRNA species and subsequently monitored for human GLA protein production. The capped mRNA species included Cap0 (unmethylated at the 2'-O position) and Cap1 (2'-O methylated)

The foregoing studies were performed using male CD-1 mice of approximately 6-8 weeks of age at the beginning of each experiment. Samples were introduced by a single bolus tail-vein injection of an equivalent total dose of 30 micrograms of encapsulated GLA, EPO, FIX or AIAT mRNA. Serum concentrations of GLA protein were determined at six hours. All animals were euthanized by $CO_2$ asphyxiation 6 hours post-dose administration (±5%) followed by thoracotomy and terminal cardiac blood collection. Whole blood (maximal obtainable volume) was collected via cardiac puncture on euthanized animals into serum separator tubes, allowed to clot at room temperature for at least 30 minutes, centrifuged at 22° C.±5° C. at 9300 g for 10 minutes, and the serum was extracted. For interim blood collection at six hours, approximately 40-50 µL of whole blood was be collected via facial vein puncture or tail snip. Samples collected from non-treatment animals were used as a baseline GLA levels for comparison to study animals. The liver and spleen of each mouse was harvested, apportioned into three parts and stored in either 10% neutral buffered formalin or snap-frozen and stored at 80° C.

Human GLA protein production was measured by enzyme-linked immunosorbent assay ("ELISA"). Standard ELISA procedures were followed employing sheep anti-Replagal G-188 IgG as the capture antibody with rabbit anti-Replagal IgG as the secondary (detection) antibody. Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device Flex Station instrument. Untreated mouse serum and human Replagal® protein were used as negative and positive controls, respectively.

Figure 3:
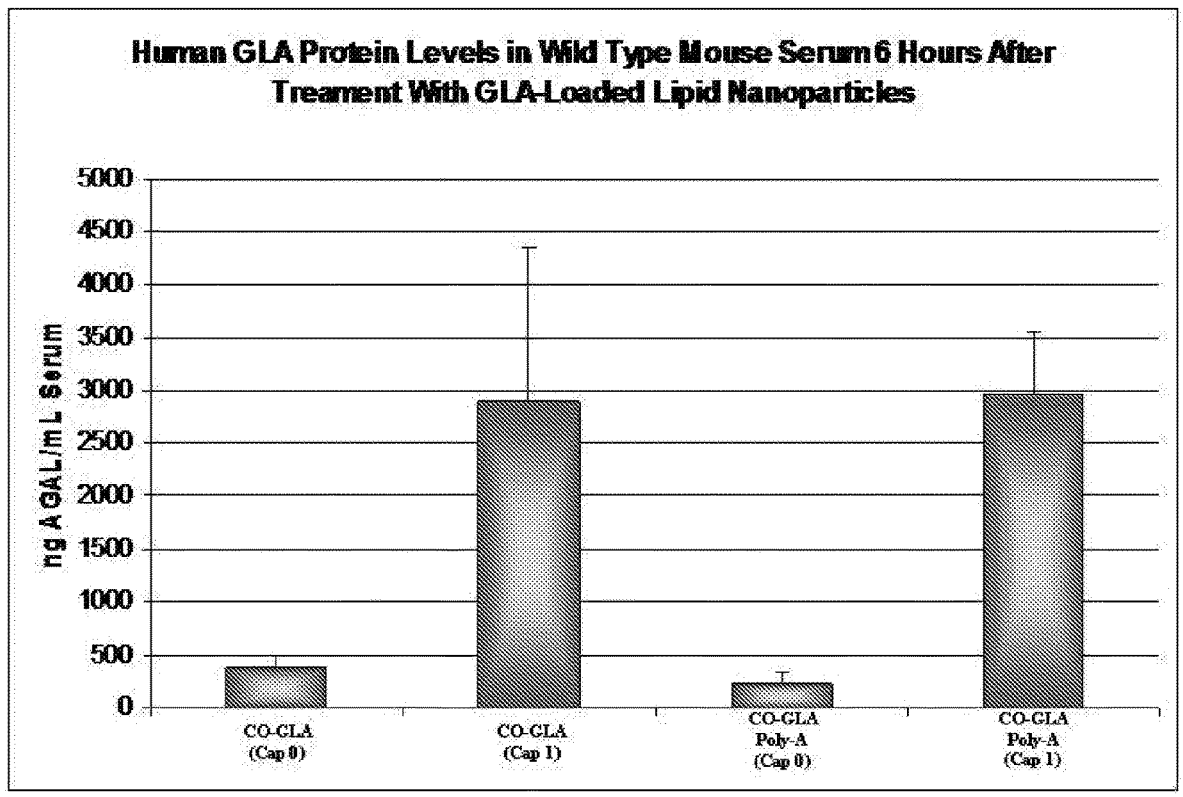
FIG. 3 is a bar graph demonstrating quantification of secreted human alpha-galactosidase (GLA) protein levels as measured via ELISA. The protein detected is a result of its production from GLA mRNA delivered intravenously via a single dose of lipid nanoparticles (30 ug encapsulated GLA mRNA) six hours post-administration.

As illustrated in FIG. 3, following the intravenous injection of capped species of CO-GLA mRNA loaded in the C12-200-based lipid nanoparticles, a substantial level of human GLA protein could be detected in mouse serum within 6 hours. Notably, there was a statistically significant increase in protein production when employing mRNA with a Cap1 structure versus that of a Cap0 structure. These results demonstrated the importance of having the ability to characterize and quantify the capping efficiency of the mRNA synthesis process.

Example 5: Cap ELISA Using Oligo dT Coated Plates

Figure 4:
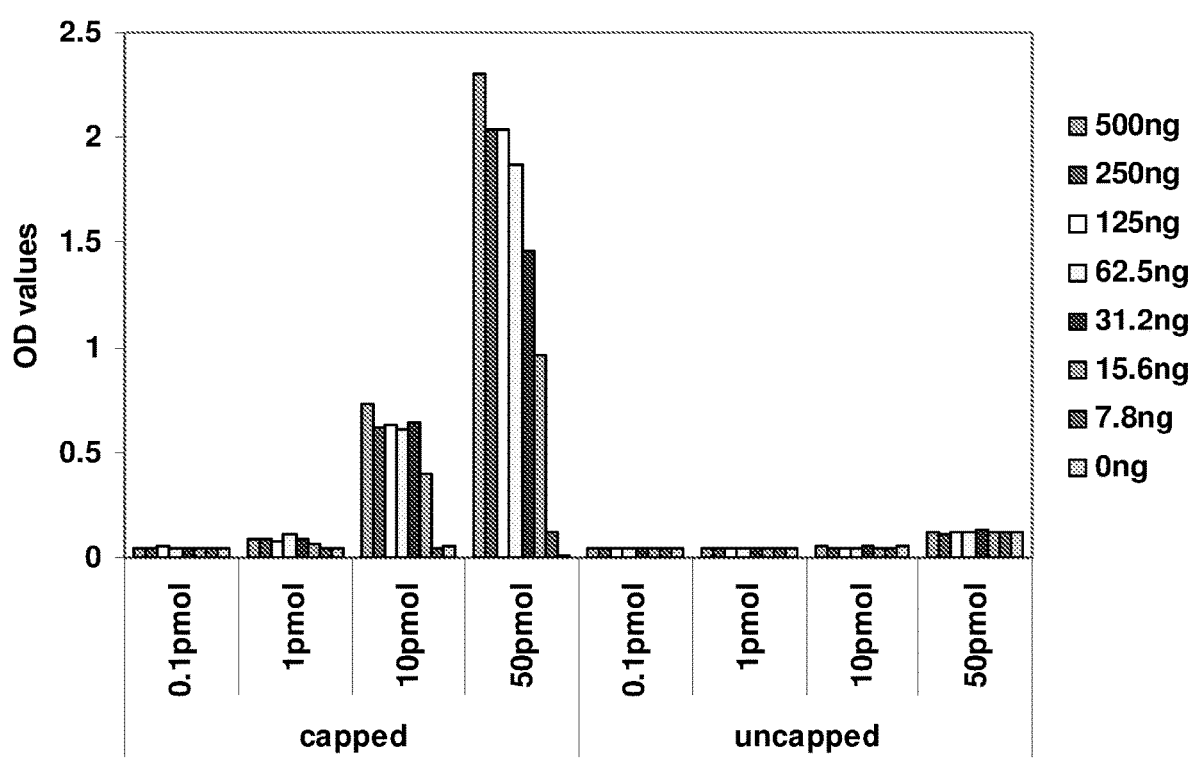
FIG. 4 shows an exemplary graph demonstrating quantification of capping in various amounts of capped and uncapped mRNA as measured by ELISA. The signal detected is derived from the interaction of the anti-cap antibody with the cap structure in the RNA samples.

This example demonstrates the use of oligo dT coated ELISA plates in capping quantification assays. Specifically, LNA enhanced oligo-T20 (Exiqon) were tested for their binding efficiency in Nunc immobilizer amino plates (Thermo Scientific) in a range from 0.1 pmol/well to 500 pmol/well in 100 □l Coating buffer buffer (50 mM $NaHCO_3$ pH 9.6). The plates were incubated for 1.5 hours rotating at room temperature, washed 3 times with 200 □l Wash buffer (1×PBS, 0.05% Tween 20) and patted dry on paper towels. The mRNA binding capacity was tested with capped/uncapped mRNA in a range from 7.8 ng/well to 500 ng/well in 100 □l Binding buffer (50 mM Sodium phosphate pH 7.0) and incubated for 90 minutes rotating at room temperature. The plates were washed 3 times with 200 □l wash buffer and patted dry on paper towels. 2 □l of anti-cap antibody (Sysy) was conjugated directly with HRP using Zenon horseradish peroxidase mouse $IgG_1$ labeling kit (Invitrogen) in a final volume of 20 □l. The HRP conjugated antibody was mixed in at 0.8 □l/ml in Blocking buffer (1×PBS, 2% BSA, 0.05% Tween 20) and added at 100 □l/well and incubated for 1 hour rotating at room temperature. The plates were washed 3 times with 200 □l binding buffer and patted dry on paper towels. TMB EIA substrate solution was prepared according to manufacturer's instructions. 100 □l of this was added to each well and incubated for 15 mins at room temperature. The reaction was stopped after 10 minutes by adding 100 □l of 2N $H_2SO_4$ and read using Molecular Devices plate reader at 450 nm. FIG. 4 shows exemplary results of quantification of capping in capped and uncapped mRNA as measured by ELISA. The signal detected is derived from the interaction of the anti-cap antibody with the cap structure in the RNA samples.

This example demonstrates that quantification of capping can be optimized using oligo dT coated ELISA plates as capturing substrates.

Example 6: Quantification of Capping Efficiency Using Oligo dT Capture ELISA

In this example, we further demonstrated that capping efficiency in various mRNA samples may be effectively quantified using oligo dT capture ELISA.

Specifically, oligo dT coated mRNA capture plates were prepared by binding 50 pmol LNA enhanced oligo-T20

Figure 5:
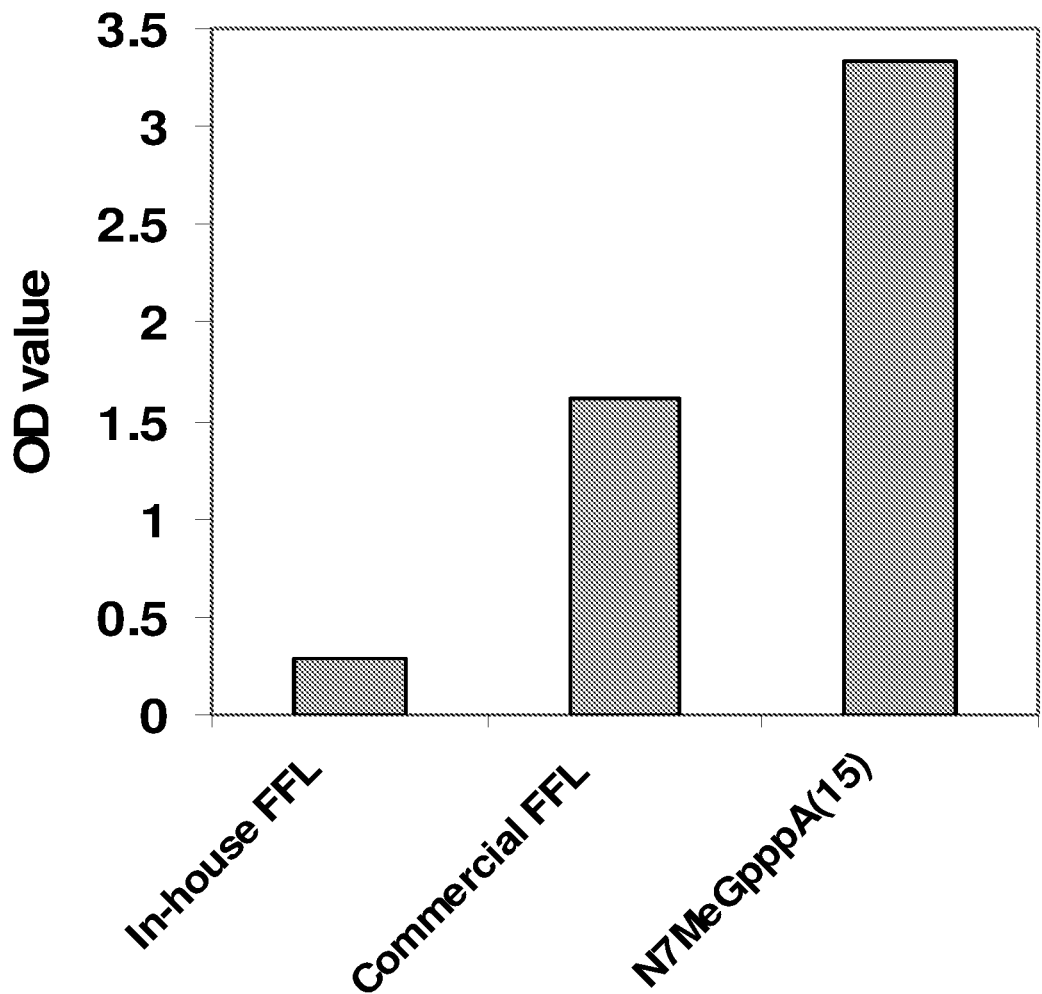
FIG. 5 shows an exemplary bar graph demonstrating quantification of capping in in-house and commercially synthesized capped mRNA along with a standard N7Methyl capped RNA as measured by ELISA. The signal detected is derived from the interaction of the anti-cap antibody with the cap structure in the RNA samples.

(Exiqon) in 100 μl Coating buffer per well in Nunc immobilizer amino plates (Thermo Scientific). The plates were incubated for 1.5 hours rotating at room temperature. The plates were washed 3 times with 200 μl Wash buffer (1×PBS, 0.05% Tween 20) and patted dry on paper towels. N7 Methyl capped oligo [N7MeGppp]-AAAAAAAAAAAAAAA was synthesized (Biosynthesis) for the standard curve measurements. 64 ng N7 Methyl capped oligo and 64 ng capped mRNA synthesized commercially with a 200 bp polyA tail or in house with a 500 bp polyA tail were added per well in 100 μl RNA binding buffer (50 mM Sodium phosphate pH 7.0) and incubated for 90 minutes rotating at room temperature. The plates were washed 3 times with 200 μl wash buffer and patted dry on paper towels. 2 μl of anti-cap antibody (Sysy) was conjugated directly with HRP using Zenon horseradish peroxidase mouse $IgG_1$ labeling kit (Invitrogen) in a final volume of 20 μl. The HRP conjugated antibody was mixed in at 0.8 μl/ml in Blocking buffer (1×PBS, 2% BSA, 0.05% Tween 20) and added at 100 μl/well and incubated for 1 hour rotating at room temperature. The plates were washed 3 times with 200 μl binding buffer and patted dry on paper towels. TMB EIA substrate solution was prepared according to manufacturer's instructions. 100 μl of this was added to each well and incubated for 15 minutes at room temperature. The reaction was stopped after 10 minutes by adding 100 μl of 2N $H_2SO_4$ and read using Molecular Devices plate reader at 450 nm. FIG. 5 shows exemplary results of quantification of capping in various mRNA samples (e.g., certain in-house Firefly Luciferase (FFL) mRNA, commercial FFL mRNA, and a standard N7Methyl capped RNA) as measured by ELISA.

This example demonstrates that ELISA (such as oligo dT capture ELISA) may be used to effectively quantify capping efficiency in mRNA samples.

Equivalents and Scope

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a", "an" and "the" may mean one or more than one unless indicated to the contrary or otherwise evident from the context. Thus, for example, reference to "an antibody" includes a plurality of such antibodies, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are presenting, employed in, or otherwise relevant to a given product or process. Furthermore, it is to be understood that the invention encompasses all variations, combinations, and permutations in which one or more limitation, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for anyone of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understand of one of ordinary skill in the art, values that are expressed as ranges can assume any specific value or sub-range within the state ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

Other Embodiments

Those of ordinary skill in the art will readily appreciate that the foregoing represents merely certain preferred embodiments of the invention. Various changes and modifications to the procedures and compositions described above can be made without departing from the spirit or scope of the present invention, as set forth in the following claims.

We claim:

1. A method of quantifying mRNA capping efficiency, the method comprising:
   a) contacting an mRNA sample comprising capped mRNA with a cap specific binding substance under conditions that permit the formation of a complex between the cap specific binding substance and the capped mRNA; and
   b) quantitatively determining the amount of the complex as compared to a standard curve prepared using a number of samples of known cap concentration, thereby quantifying mRNA capping efficiency.

2. The method of claim 1, wherein the cap has a structure of formula I:

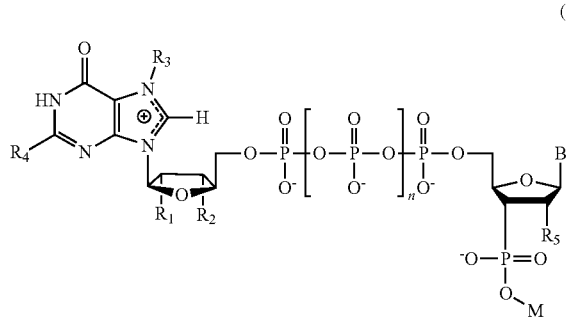

(I)

wherein,
B is a nucleobase;
$R_1$ is selected from a halogen, OH, and $OCH_3$;
$R_2$ is selected from H, OH, and $OCH_3$;
$R_3$ is $CH_3$, $CH_2CH_3$, $CH_2CH_2CH_3$ or void;
$R_4$ is $NH_2$;
$R_5$ is selected from OH, $OCH_3$ and a halogen;
n is 1, 2, or 3; and
M is a nucleotide of the mRNA.

3. The method of claim 2, wherein the nucleobase is guanine.

4. The method of claim 1, wherein the cap is a $m^7G$ cap with a structure of formula II:

wherein,
$R_2$ is H or $CH_3$;
$R_4$ is $NH_2$;
$R_5$ is OH or $OCH_3$;
$R_6$ is H or $CH_3$; and
M is a nucleotide of the mRNA.

5. The method of claim 1, wherein the cap specific binding substance is a cap specific binding protein selected from the group consisting of eukaryotic initiation factor 4E (eIF-4E), nuclear cap-binding protein subunit 1, nuclear cap-binding protein subunit 2, and nuclear cap-binding complex.

6. The method of claim 1, wherein the cap specific binding substance is a cap specific antibody.

7. The method of claim 6, wherein the cap specific binding substance is an anti-$m^7G$ antibody.

8. The method of claim 1, wherein the step of quantitatively determining the amount of the complex comprises measuring a detectable signal associated with the complex.

9. The method of claim 8, wherein the detectable signal is a fluorescent signal, a colorimetric signal or a radioactive signal.

10. The method of claim 1, wherein the samples of known cap concentration comprise an mRNA sample with a predetermined amount of capped mRNA.

11. The method of claim 1, wherein the samples of known cap concentration comprise a predetermined amount of synthesized cap.

12. The method of claim 1, wherein quantifying mRNA capping efficiency comprises quantifying the absolute amount of capped mRNA in the mRNA sample.

13. The method of claim 1, wherein quantifying mRNA capping efficiency comprises quantifying the percentage of capped mRNA in the mRNA sample.

14. The method of claim 1, wherein the method further comprises a step of capturing the mRNA on a substrate.

15. The method of claim 14, wherein the mRNA is captured by a poly-T oligo that binds to the poly-A tail of the mRNA.

16. The method of claim 14, wherein the mRNA is captured by a poly-A binding protein or antibody.

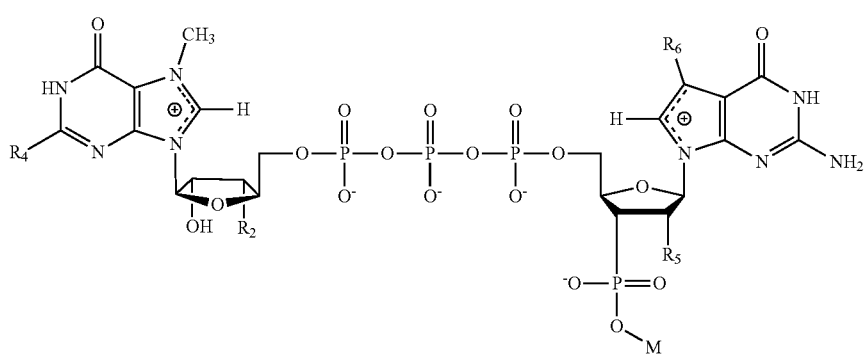

(II)

17. The method of claim 14, wherein the substrate is a microplate, magnetic bead, particle, polymeric bead, chromatographic resin, filter paper, nitrocellulose, diazocellulose, glass, latex, polystyrene, polyvinylchloride, propylene, polyethylene, dextran, Sepharose, agar, starch, nylon, silica gel, or hydrogel.

18. The method of claim 14, wherein the substrate is coated with avidin or streptavidin.

19. The method of claim 18, wherein the mRNA is captured by a poly-oligo that binds to the poly-A tail of the mRNA or by a poly-A binding protein or antibody, and wherein the poly-T oligo or the poly-A binding protein or antibody is biotinylated.

20. The method of claim 1, wherein the mRNA sample is synthesized in vitro.

21. The method of claim 1, wherein the mRNA sample comprising capped mRNA is provided in an amount less than 500 ng.

* * * * *

UNITED STATES PATENT AND TRADEMARK OFFICE
CERTIFICATE OF CORRECTION

Page 1 of 1

| | |
|---|---|
| PATENT NO. | : 12,421,538 B2 |
| APPLICATION NO. | : 18/430247 |
| DATED | : September 23, 2025 |
| INVENTOR(S) | : Frank DeRosa et al. |

It is certified that error appears in the above-identified patent and that said Letters Patent is hereby corrected as shown below:

On the Title Page

Item (12): delete "Derosa et al." and insert -- DeRosa et al. --.

Item (72) Under Inventors: "Derosa" should be -- DeRosa --.

In the Claims

At Column 41, Line 10: "poly-oligo" should be -- poly-T oligo --.

Signed and Sealed this
Sixteenth Day of December, 2025

John A. Squires
*Director of the United States Patent and Trademark Office*